(12) United States Patent
Costantino et al.

(10) Patent No.: US 9,519,724 B2
(45) Date of Patent: Dec. 13, 2016

(54) TEMPORARY CUTANEOUS INFORMATION DEVICE AND ASSOCIATED METHOD AND MULTI-PATIENT TREATMENT INFRASTRUCTURE

(71) Applicants: Peter Costantino, Westport, CT (US); Laurie Costantino, Westport, CT (US); Michael Gilvary, Westport, CT (US); Anthony H. Handal, Westport, CT (US)

(72) Inventors: Peter Costantino, Westport, CT (US); Laurie Costantino, Westport, CT (US); Michael Gilvary, Westport, CT (US); Anthony H. Handal, Westport, CT (US)

(*) Notice: Subject to any disclaimer, the term of this patent is extended or adjusted under 35 U.S.C. 154(b) by 0 days.

(21) Appl. No.: 14/862,033

(22) Filed: Sep. 22, 2015

(65) Prior Publication Data

US 2016/0103962 A1  Apr. 14, 2016

Related U.S. Application Data

(63) Continuation of application No. PCT/US2015/051289, filed on Sep. 22, 2015.

(60) Provisional application No. 62/053,725, filed on Sep. 22, 2014.

(51) Int. Cl.
| | |
|---|---|
| G06F 17/00 | (2006.01) |
| G06F 17/30 | (2006.01) |
| G06K 19/077 | (2006.01) |
| G06K 19/04 | (2006.01) |
| G06F 19/00 | (2011.01) |

(Continued)

(52) U.S. Cl.
CPC ....... *G06F 17/30879* (2013.01); *G06F 19/323* (2013.01); *G06K 7/1447* (2013.01); *G06K 19/041* (2013.01); *G06K 19/0776* (2013.01); *G06K 19/07722* (2013.01); *G06K 19/07749* (2013.01); *G06Q 50/12* (2013.01)

(58) Field of Classification Search
USPC ............................ 235/375, 385, 462.01, 488
See application file for complete search history.

(56) References Cited

U.S. PATENT DOCUMENTS

| | | |
|---|---|---|
| 6,201,662 B1 | 3/2001 | Graves |
| 7,758,080 B1 * | 7/2010 | Vidler .................... B42D 15/00 283/81 |
| 7,798,404 B2 | 9/2010 | Gelbman |

(Continued)

*Primary Examiner* — Ahshik Kim
(74) *Attorney, Agent, or Firm* — Handal & Morofsky LLC

(57) ABSTRACT

Apparatus for identifying and providing for the retrieval of information relating to an individual, comprises an adhesive layer and a machine readable device secured to said adhesive layer. The machine readable device is encoded with identification information. A first quantity of ink deposited on said adhesive layer is arranged to provide a physiologically perceptible and humanly understandable visual indication of information relating to set individual. The adhesive layer, the machine readable device and said first quantity of ink form an individual identification device. The machine readable device is secured to said adhesive layer further comprises a second quantity of ink deposited on said adhesive layer and arranged to provide a machine readable image. A plurality of reader devices and said individual identification device provide information respecting the individual identified by said individual identification device to a computer system which includes a memory with an algorithm for processing collected information.

8 Claims, 23 Drawing Sheets

(51) Int. Cl.
  *G06K 7/14* (2006.01)
  *G06Q 50/12* (2012.01)

(56) References Cited

U.S. PATENT DOCUMENTS

| | | |
|---|---|---|
| 8,408,602 B2 | 4/2013 | Berson |
| 2003/0183695 A1 | 10/2003 | Labrec |
| 2003/0217489 A1 | 11/2003 | Witkowski |
| 2003/0226897 A1 | 12/2003 | Jones |
| 2004/0091659 A1 | 5/2004 | Banks |
| 2005/0171787 A1 | 8/2005 | Zagami |
| 2006/0031099 A1 | 2/2006 | Vitello |
| 2006/0037502 A1 | 2/2006 | Warther |
| 2006/0248767 A1* | 11/2006 | Hofer .................. A61L 15/46 40/633 |
| 2007/0029377 A1 | 2/2007 | Hinckley |
| 2008/0208236 A1* | 8/2008 | Hobbs ............... A61M 39/0208 606/186 |
| 2008/0275327 A1 | 11/2008 | Faarbaek |
| 2010/0271180 A1 | 10/2010 | Oberle |
| 2011/0081522 A1 | 4/2011 | Kim |
| 2011/0096388 A1 | 4/2011 | Agrawal |
| 2011/0303344 A1 | 12/2011 | Bortel |
| 2013/0149508 A1 | 6/2013 | Kwak |
| 2014/0008441 A1 | 1/2014 | Huynh |
| 2014/0035720 A1 | 2/2014 | Chapman |
| 2015/0053759 A1* | 2/2015 | Cahill, Jr. ........ G06K 19/06009 235/380 |

* cited by examiner

TEMPORARY CUTANEOUS INFORMATION DEVICE AND ASSOCIATED METHOD AND MULTI-PATIENT TREATMENT INFRASTRUCTURE

CROSS REFERENCE TO RELATED APPLICATIONS

This application claims the benefit of Provisional Patent Application No. 62/053,725, filed Sep. 22, 2014, and PCT Application No. PCT/US15/51289 filed Sep. 22, 2015, the disclosures of which are hereby incorporated herein by reference thereto.

TECHNICAL FIELD

The invention relates to apparatus and methods for tracking and regulating patient care in a medical facility.

STATEMENT REGARDING FEDERALLY SPONSORED RESEARCH OR DEVELOPMENT (Not applicable)

BACKGROUND OF THE INVENTION

Today, notwithstanding very significant advances in many sectors of the health-care industry, the inability to quickly identify patients accurately and durably continues to result in numerous incidents which, one would think, should be avoidable. Consequences may include medication error, transfusion errors, medication errors, mistaken phlebotomies, surgery errors, financial and other issues, testing errors, wrong person procedures, and the discharge of infants to the wrong families. Numerous incidents are reported every year with patient misidentification cited in individual root cause analyses, such as that conducted by the United States Department of Veterans Affairs (VA) National Center for Patient Safety. Nevertheless, despite availability of numerous products and strategies designed to reduce the risk of patient misidentification and the consequences of such incidents, the problem persists.

Current methodology for the identification of patients at medical facilities generally involves the use of a wrist bracelet. Problems with current band methods of identification include interference with intravenous insertion, in the need to remove during certain procedures situations, the fact that such bands are uncomfortable, and the possibility of their presenting a hazard. Such bands also carry limited information, sometimes making necessary additional devices.

Moreover, continuing pressures to limit hospital staff working hours increases the risk of such errors, due to the increased number of staff nurses, technicians, residents and other doctors caring for each patient. Thus, increased handover and other communication risks are increased as current medical care strategies evolve. Also significant is the likelihood that changes in medicine due to the implementation of the affordable care act and increasing political involvement in the medical system will create pressures that will increase the likelihood of misidentification incidents.

Given the longstanding high profile recognition that patient misidentification is a serious problem, numerous solutions have been proposed, including barcoding, color coding of patient wristbands, use of multiple identification strategies, and venous pattern recognition systems. Many of these solutions seek to improve patient care by including additional information at the point of care. More recent suggestions involve the use of RFID technology.

Likewise, numerous tagging technologies have long been available, diversely ranging from approaches as simple as the number on a ball player's jersey to technologies as sophisticated RFID tagging, and including such things as rubber stamp applied ink markings on the wrists of concert-goers, bracelets and nametags for convention attendees, branding of cattle, temporary cutaneous identification device (so-called temporary tattoos) warning of allergies and printed adhesive tags for visitors to buildings with a name, a picture and the identification of an organization being visited.

However, despite the availability of such a wide range of tagging and identification systems, despite their drawbacks and limitations, simple alphanumeric patient identification wristbands remain the only significant method employed for identification of patients. Other tagging and identification systems face significant obstacles to implementation in the context of a multi-patient medical facility. Color coding of patient wristbands is of limited value, given the relatively limited palette available. Color coding has also not been adopted due to a relatively high likelihood of causing misinformation to be perceived by medical care staff. Barcoding schemes require significant and expensive hardware at the point of care. Moreover, in critical situations, delays caused by the absence of immediate availability of barcode reading equipment can result in unacceptable delay. Even after barcode reading equipment has been accessed, system delays may delay access to information. Likewise, other methodologies such as RFID, and use of the veins of the patient on a part of the body such as the back of the hand as a fingerprint-type identifier, also involve delays while appropriate equipment is accessed and while that equipment accesses data.

Current RFID, barcode and physiology pattern recognition systems can also suffer from relatively large startup costs, and yield little information or no information beyond identification. This combined with the fact that various types of accessibility/system failures may introduce new errors, such systems have not seen widespread adoption. Thus, despite all their problems, as noted above, and even the potential of providing a choking hazard to newborns, nevertheless, patient wristbands including only a minimal amount of information remain, by an overwhelming majority, the dominant patient identification system currently in use.

SUMMARY OF THE INVENTION

In accordance with the invention, a method and a temporary cutaneous identification device for identifying patients is provided.

In accordance with one embodiment of the invention, the temporary cutaneous identification device includes a barcode which may be read by a smart phone with an appropriate application which allows both 1) the input of data and 2) the retrieval of additional information either by direct request for keyword searching. This enables the generation of more complete patient record at a central server. At the same time, artificial intelligence software on a computing device with the capability of accessing the central server database periodically checks patient conditions, measurements, medications, procedures and so forth to identify potential issues, inconsistencies, and other circumstances suitable for bringing to the attention of different types of medical personnel. More particularly, it is contemplated that certain conditions might be brought to nursing staff, while other circumstances might result in information being sent to resident physician in the unit of the hospital where the patient is located, while still other circumstances will also be copied to the surgeon, anesthesiologists, or referring physician.

BRIEF DESCRIPTION OF THE DRAWINGS

The operation of the inventive apparatus and method will become apparent from the following description taken in conjunction with the drawings, in which.

DETAILED DESCRIPTION OF THE PREFERRED EMBODIMENTS

Figure 1:
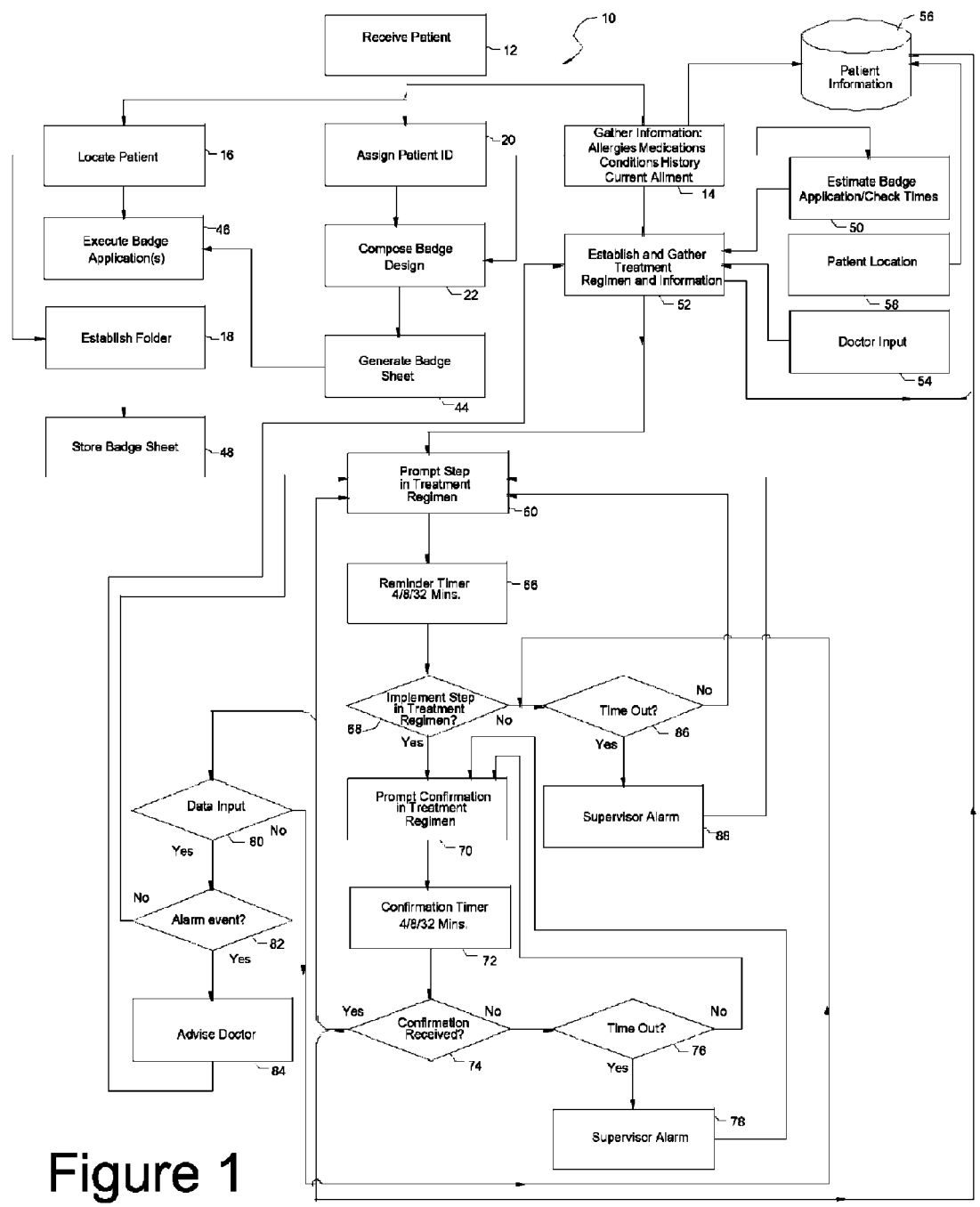
FIG. 1 is a flow chart generally illustrating a general implementation of the present invention.

Turning to FIG. 1, the method 10 of the present invention may be understood. Initially, a patient is received at step 12. At this point, information is gathered from the patient at step 14, including such things as allergies, current medications, current conditions, history and the particular problem that has brought the patient to the facility. In accordance with the invention, the inventive temporary cutaneous identification device may be applied to the patient as more fully appears herein. Thus, for example, the inventive temporary cutaneous identification device may be applied in the admitting area of the hospital emergency room, or surgical center. At about this time, at step 16 the patient would be assigned a treatment point in the hospital, for example a particular bed or room.

When the patient is located, a folder for receiving the patient's medical records is established at step 18. For example, this may be a simple folder which is attached to the bed of the patient, and is meant as a point of treatment information center. The folder should have basic patient identification, including name and a patient identification number established at step 20. The identification number assigned at step 20 together with information gathered at step 14 is then sent to a central storage point, for example, or a plurality of storage points, dependent upon the infrastructure of the facility where the inventive method is being implemented. Ideally, such information is stored in a central server for regular update and for providing such information in response to information retrieval requests, as appears more fully hereinbelow.

The information collected at step 14 may, optionally, include such information as patient allergies, current medications, chronic conditions, and medical history. Likewise, family history with respect to conditions likely to present risks to the patient, such as diabetes, heart disease, Parkinson's disease, and so forth, are also gathered at step 14. In addition, the patient's reason for coming in for medical treatment is also gathered at step 14 for entry into, for example, the single database.

In accordance with the invention, it is also contemplated that additional information may be gathered at the point of admission or shortly thereafter, such as patient height, weight, blood pressure, and so forth. Such information is also stored in the database for subsequent updating and retrieval. Likewise, existing information in the database of the hospital may be automatically retrieved at the time of patient admission and, where appropriate the information may be presented for patient verification.

After basic information has been gathered from the patient and stored in the appropriate database, the patient is located at a point of treatment at step 16. Either immediately or at a subsequent appropriate point, a patient badge design is generated at step 22. In accordance with the invention, the patient badge may comprise a selection of information taken from information gathered at step 14. As the information about the patient is gathered and sent to the central database, revised patient badges may be generated.

In accordance with one embodiment of the invention, patient badges for all patients in the system will include the same types of information in the same places. One field on the patient badge may be reserved for special information particular or important with respect to the treatment of a particular patient. The invention also contemplates that information on a patient badge may be shown in type scaled to the size of the patient badge, which may, in turn, be scaled to the size of the patient. This information may be gathered from the age of the patient, and the sex the patient. Alternatively, or additionally, as additional information is input into the system, patient badge size may be scaled to actual height and/or weight information. It is contemplated that optimal size for the inventive temporary identification device is approximately 4.0-4.5 cm wide and 5.0 cm in vertical height, however badges 3.0-8 cm wide and 3.5 to 10 cm in vertical height will work well.

In accordance with one embodiment of the invention, one or multiple diecut sheets, similar to the sheets used with printers making temporary tattoos, may be used. Different diecut sheets may be provided for patient badges of different sizes, in much the same manner as different diecut labels are provided for generation of labels in manufacturing and office applications. Sheets for printing up the inventive temporary cutaneous identification device may be made with badge shapes preprinted on them, diecut with badge shapes for easy use, or perforated for separation from each other into temporary cutaneous identification devices—Extra inventive temporary cutaneous identification devices printed on a sheet can be placed in the patient's chart for future use.

In accordance with another preferred embodiment of the invention, the composition of a patient badge design will depend upon the particular information to be displayed for the patient who is to wear the patient badge. In such a case patient badges may be provided where there are a variable number of informational indications printed on the patient badges. Some patients may require a relatively small number of items of information. Other patients may have multiple allergies, and other characteristics which should be displayed on a patient badge. Where there are a large number of items of information which are important enough to put on a patient badge, smaller type may be used in order to fit all the information on the patient badge. Alternatively, if there is a small amount of information for the patient badge, relatively large type may be used. More important information may be emphasized by using large type and/or another device, such as color. For example, a serious but uncommon allergy might be displayed in large type in red.

In this embodiment of the invention, at step 22, an algorithm which receives such information may include weighting factors for determining relative importance of various items of information and scale alphanumeric indications of the same in accordance with the importance, and assign appropriate colors to enhance detectability of this information.

On the other hand, it may not be possible to include all desirable and/or important information on a single patient badge, and in accordance with another embodiment of the invention, such information may be put on a separate additional patient badge. In accordance with a preferred embodiment of the invention, such additional tag is of a different shape, thus facilitating directing the healthcare provider to primary and secondary information. Likewise, the provision of two patient badges with different shapes, reduces the mental overhead and lessens the likelihood of distraction associated with being sure that both patient badges are reviewed by the healthcare provider, whether he or she be a doctor, nurse or other facility personnel.

In accordance with the invention, it is also contemplated that patient badge composition design performed at step 22 may include color and pattern selections, for example, as discussed in detail below.

Figure 2:
FIG. 2 is a diagram illustrating a plurality of patient badges generated on a single sheet.

In accordance with the invention, it is contemplated that a plurality of patient badges will be generated on a single sheet of, for example, paper 23, as illustrated in FIG. 2. In this figure, patient badges 24 are scaled for a sheet of patient badges 24 having a dimension of 11"×17". 8½ by 11 inch, and A4 size paper is also suitable for the inventive badge sheet. Sheet 23 includes a number of individual patient badges 24, which may be printed on a sheet of paper 23, carries a number of patient badges which may be used individually by application in the manner of a temporary cutaneous identification device. Such patient badges may be cut out with scissors. Alternatively, diecutting 28 may be used to allow them to be individually removed from the sheet without the aid of scissors.

Figure 3:
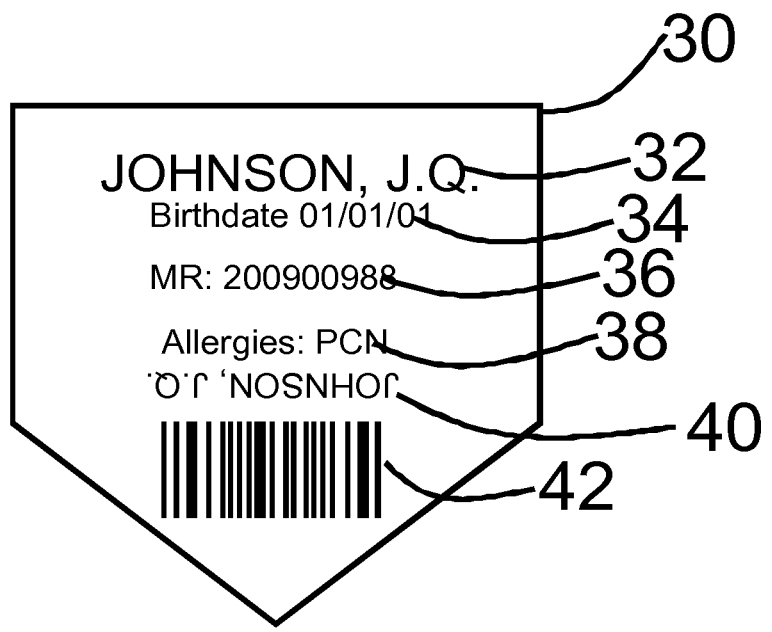
FIG. 3 illustrates a single patient badge with alphanumeric content in diagrammatic form.

Referring to FIG. 3 (which shows alphanumeric content in diagrammatic form apart from an actual patient badge), each patient badge 30 includes the name 32 of the patient, and the patient's date of birth 34. A patient ID number 36 also appears on the patient badge. In the example given in FIG. 3, allergies are indicated at position 38. In this case the letters "PCN" indicate a penicillin allergy. The name of the patient is repeated upside down at position 40, to facilitate reading of the name regardless of the position of the patient relative to the medical caregiver observing the patient badge. Optionally, the patient badge also includes an optically readable code 42. Alternatively, optically readable code 42 may be replaced by any automated readable device, such as an RFID chip, a quad code, and so forth. Moreover, it is noted that the system may accommodate OCR capability which would make the generation of a machine-readable code, such as code 42, unnecessary, because the system could simply read the same information that a human operator reads.

In accordance with the invention, patient badges are generated using technology of the types used to generate temporary tattoos. Thus, the patient badges essentially comprise an adhesive layer with an image formed of an ink deposit overlying the adhesive layer. After application, the result is an ink image glued to the skin by the adhesive. Accordingly, after patient badges are generated at step 44 using the patient badge design generated by the system at step 22, the patient badges are applied to the patient at step 46. The inventive temporary cutaneous identification device is easy to remove, hypo allergenic and suitable for pregnant women and children. It is easily removed using mineral oil.

Figure 4:
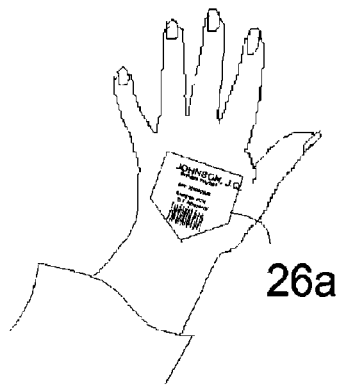
FIG. 4 is a diagram depicting a patient badge applied to the back of the hand of a patient.
Figure 5:
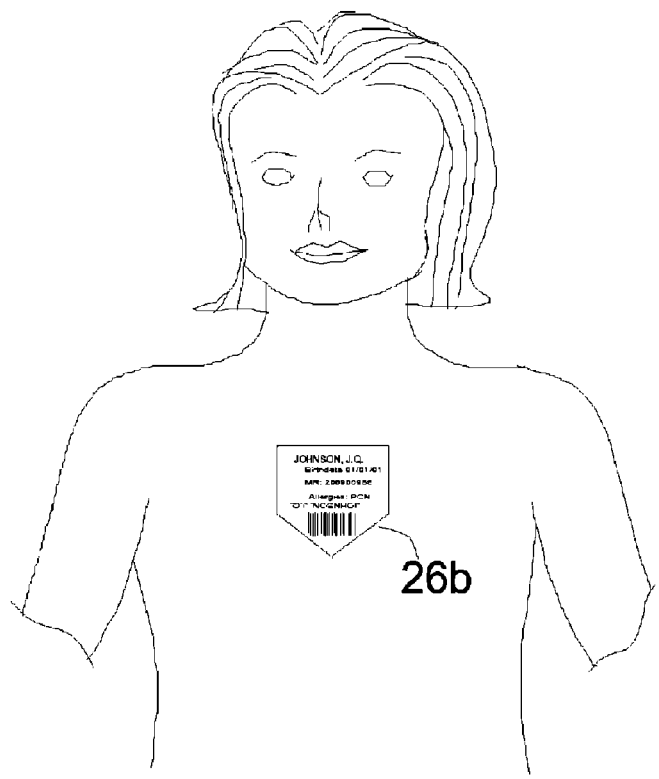
FIG. 5 is a diagram depicting a patient badge applied to an area of the chest of a patient directly beneath the throat.
Figure 6:
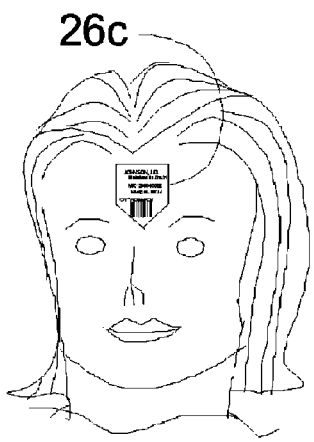
FIG. 6 is a diagram depicting a patient badge applied to the forehead of a patient.
Figure 7:
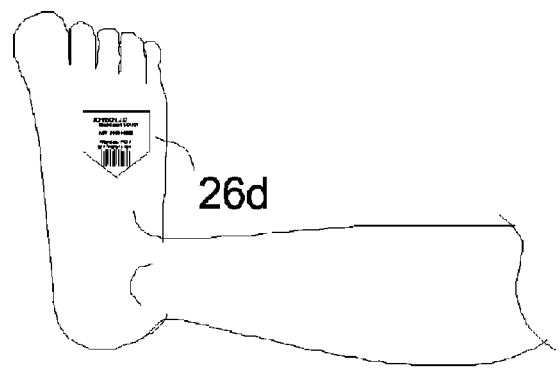
FIG. 7 is a diagram depicting a patient badge applied to the top surface of the foot.

Application of a patient badge to a patient at step 46 may be made to the back of the hand of the patient (FIG. 4, applied patient badge 26a), to the area of the chest of the patient directly beneath the throat (FIG. 5, applied patient badge 26b), to the forehead (FIG. 6, applied patient badge 26c) or to the top surface of the foot (FIG. 7, applied patient badge 26d). In accordance with the invention, it is contemplated that different sized patient badges may be used for larger and smaller people. Likewise, it is contemplated that different sized patient badges will be used in different parts of the body. For example a larger patient badge would be used on the chest of an individual, as illustrated in FIG. 5, while a relatively small patient badge might be used on the wrist.

Other locations include the upper arm on adults and center chest on newborns. In the case of young children, the posterior may be appropriate. No intravenous devices are placed at those sites and they are readily visible, and have a large enough surface area.

Figure 8:
FIG. 8 is a diagram illustrating a plurality of patient badges generated on a single sheet where badges come in various sizes of small, medium, or large.
Figure 9:
FIG. 9 is a diagram illustrating a plurality of patient badges generated on a single sheet where sizes of badges are adapted for a tween-age child patient.

Thus, in accordance with the invention, it is contemplated that a sheet of patient badges would include patient badges in, for example, large, small and medium sizes, as illustrated in FIG. 8. Similarly, a sheet of patient badges for a tween-aged child would have a plurality of patient badges of different sizes, but all scaled-down to match the size of the child. A sheet of patient badges (for example scaled for printing on a sheet having a size of 11"×17") for such a tween-age child is illustrated in FIG. 9.

Alternately, patient badges may be applied to multiple positions on the patient, or on another part of the patient's skin, as the doctor or health care facility may determine to be appropriate for the particular type of treatment which the patient is expected to receive.

Referring back to FIG. 1, after the patient badge has been applied to the patient, patient badge sheet 24 with the remaining unused patient badges on it is deposited in the folder at step 48, for example a folder attached to the patient's bed for the purpose of facilitating application of additional patient badges, for example as replacement patient badges due to deterioration in the condition of an applied patient badge 26 previously applied to a patient's skin.

The time interval between the successive applications of patient badges to a patient may be estimated using, for example, the information input at step 14. Such estimation may be done at step 50. Such estimation becomes part of the treatment regimen for the patient which is established at step 52. Medically related aspects of the treatment regimen are, in accordance with the preferred embodiment of the invention, established by a doctor at step 54.

In accordance with a preferred embodiment of the invention, the treatment regimen is stored at step 56, together with information gathered at step 14, the patient location input at step 58, and the treatment regimen established and gathered at step 52. Likewise, as information is changed and accumulated, the same is stored by the system returning to step 56, as appears more fully below.

In accordance with a preferred embodiment of the invention, information stored at step 56 is used to prompt, at step 60, individuals providing health care at the facility to provide various services, such as patient badge replacement, blood pressure measurements, body temperature measurements, administration of nutrition and/or drugs, and so forth. Such prompting may be done by any number of means, such as a handheld mobile device sounding an alarm and presenting an on-screen prompt for a particular service to be provided.

Figure 10:
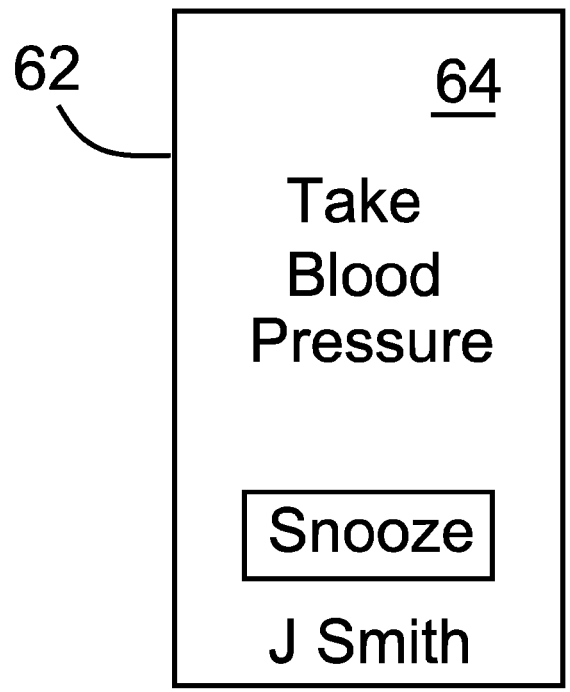
FIG. 10 is a diagram illustrating a display of a mobile device prompting the healthcare provider to do a particular task, such as taking the blood pressure of a patient.

More particularly, as illustrated in FIG. 10, the display of mobile device 62 may present an image 64 prompting the healthcare provider to take the blood pressure of the patient. Likewise, image 64 may include a touch sensitive button labeled "Snooze" which allows the healthcare provider to inform the system that the message has been received. In the case of the provision of a prompt to do an act which when completed will result in an entry into the system and will so inform the system. In accordance with a preferred embodiment of the invention, an identifier, such as the name of the patient, in the illustrated example "J Smith", is presented in image 64.

After the system has presented the prompt of FIG. 10 at step 60, by presentation of image 64, the pressing of the touch sensitive area labeled snooze causes the system to proceed to step 66, where a reminder timer is measured by the system as it is directed for a particular period of time by an algorithm resident on the central processing unit of the system running the inventive process. Alternatively, if the snooze button is not pressed, the audio alarm continues to ring until the alarm is acknowledged by the care provider.

Figure 11:
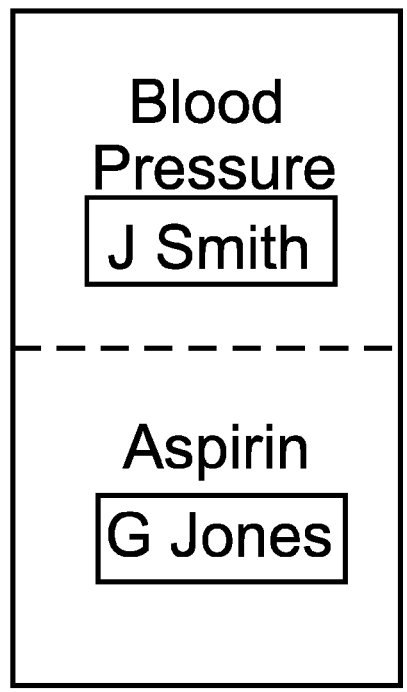
FIG. 11 illustrates a mobile device display that indicates a menu of tasks awaiting performance.

After receiving the prompt, it is contemplated that the healthcare provider will perform the particular task required, such as a measurement of blood pressure. When this occurs, the healthcare provider activates the mobile device to present a menu of tasks awaiting performance. Such a menu is illustrated in FIG. 11, showing a blood pressure task for Jean Smith and an aspirin administration for Gail Jones. If the healthcare provider wishes to take care of Jean Smith, the touchscreen touch sensitive display button "J Smith" is pressed causing the device to present the screen of FIG. 12. On this screen, fields are provided for receiving the particular information needed to be input into the system, in this case the systolic and diastolic blood pressure measurements for Jean Smith. Information may be input into the system using the touch sensitive keys of virtual keyboard 67.

Figure 12:
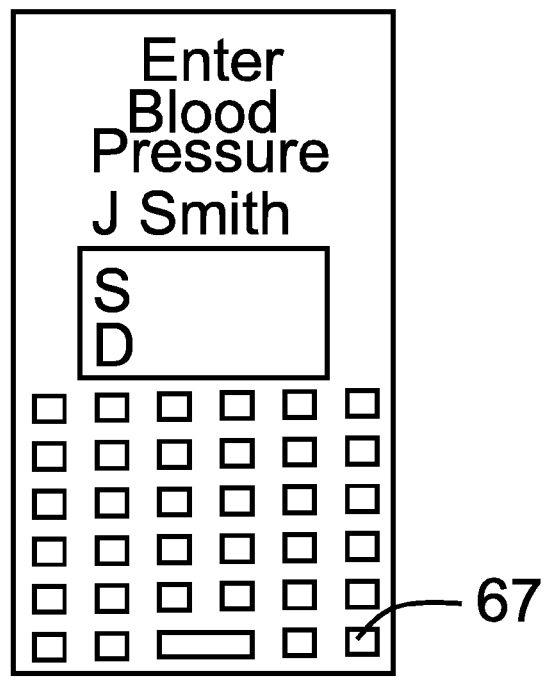
FIG. 12 illustrates a mobile device display where fields are provided for receiving particular information needed to be input into the system.
Figure 13:
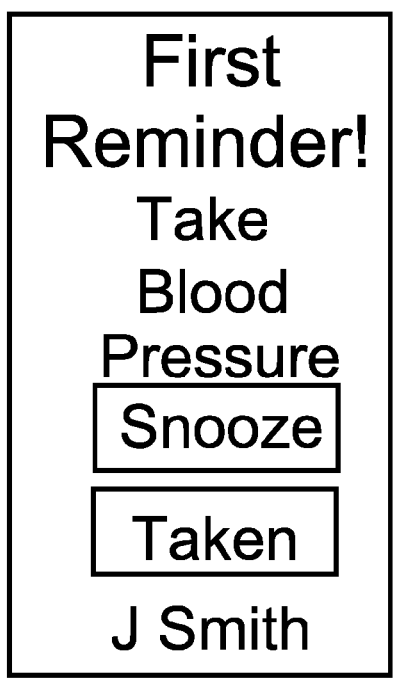
FIG. 13 illustrates a mobile device display that indicates a number of reminders a healthcare provider has and the urgency of the need to perform the particular task.

If, however, the healthcare provider does not call up the screen of FIG. 12, when the time measured at step 66 is up, a reminder prompt is presented at step 68, by presentation of the screen of FIG. 13. It is noted that the screen of FIG. 13 indicates the number of the reminder in order to indicate to the healthcare provider the urgency of the need to perform the particular task. Such timeout measurement and reminder prompts may be repeated until the task is performed.

In the case of certain tasks, such as the administration of a medicine, there is no number or other informational entry. In such cases, confirmation of the particular task having been performed may be necessary. Accordingly, at step 70, the system will present a reminder prompt. The system then proceeds to step 72 where a reminder period is measured. At the end of the reminder period, The system proceeds at step 74 to determine whether confirmation of the performance of a particular task has been received. If confirmation has been received, the system returns to the treatment plan to prompt the next task required by the plan. Such plan may be amended from time to time by the doctor responsible for the patient.

If, at step 74, no confirmation of the performance of the task has been received, the system determines at step 76 whether a longer period of time has elapsed since the original prompt to perform the particular task. If that longer period of time has not elapsed, the system proceeds to step 72 and begins the process for another reminder. However, if, at step 76, that longer period of time has elapsed, for example a period of time three times as long as the reminder time period (or a longer time period or shorter time period as may be determined by the system depending upon the nature of the task required), the system proceeds to step 78 where an alarm is sent to a supervisor's mobile device or workstation. That alarm includes enough information to allow the supervisor to identify the patient, the healthcare provider assigned to the task, and the nature of the particular task needing to be performed.

In accordance with the invention it is contemplated that the system may assign tasks to various personnel located at a point of care in accordance with such factors as the identity of the particular healthcare provider who attended to the patient previously, the nature of the task in specialized skills needed therefore, the availability and workload of personnel on hand at the point of care, and so forth.

When a task is performed, the patient badge may be scanned to assure a proper input to the system database. A smartphone or dedicated mobile device may be used to perform this task.

If, at step 74, confirmation of the performance of the task is received, this information is stored with patient information by returning to step 56. Likewise, if the particular task to be performed involves a gathering of data or other information, the system also proceeds to step 80, where, if data has been input, a determination is made at step 82 as to whether the particular indication is of a nature which suggests that the same should be reported to the doctor responsible for the patient. If the same is deemed desirable, such information is reported to the responsible doctor at step 84, by that doctor's mobile device or other communication facility.

In accordance with the invention, as illustrated in FIG. 1, it is contemplated that the system will provide prompts at step 60, reminders at step 66 and repeat reminders by determination at step 86 returning to the prompt of step 60 if a longer than normal or inordinate amount of time has not elapsed. However, if, at step 86 an inordinate amount of time has elapsed, a supervisor is alerted at step 88. The sequence may optionally be in addition to the provision for supervisor intervention at step 78. Likewise, in accordance with the invention, supervisor intervention may be limited to intervention in the event of a failure to perform the task or a failure to provide a confirmation.

Figure 14:
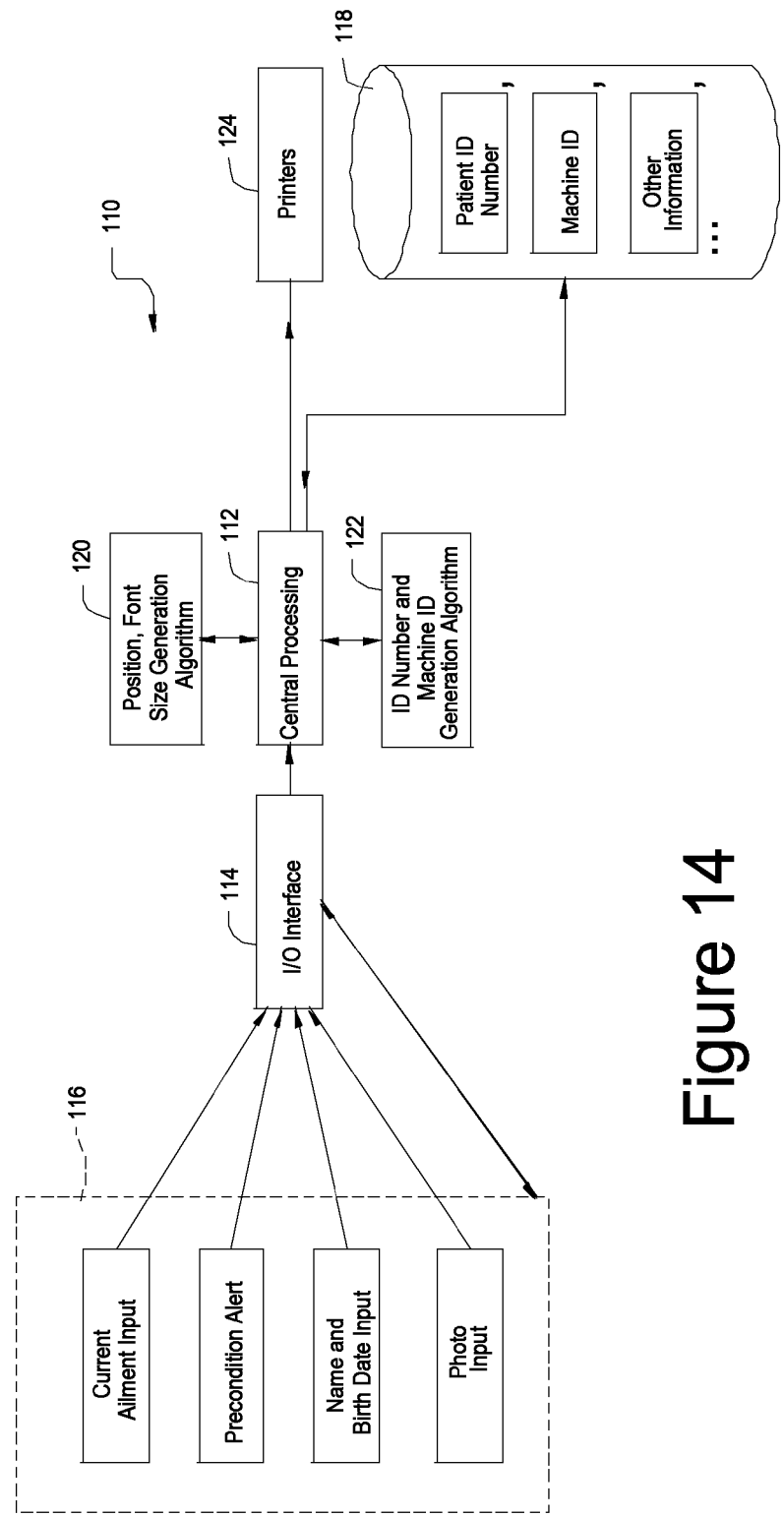
FIG. 14 is a flow chart of a system that gathers and stores patient information.

Turning to FIG. 14, the gathering and storage of information by the system may be more clearly understood. More particularly, the system 110 comprises a central processing unit 112 which communicates with system inputs via an interface 114. Interface 114 is, in turn, provided with information by various inputs devices such as a mobile device 116, which may be provided to input various types of alphanumeric information and, for example, a photograph of the patient. This information is then stored in database 118. Database 118 also is provided by central processing unit 112 with patient badge design information generated by patient badge design algorithm 120 which may be accessed by central processing unit 112. Such patient badge design information is also stored in database 118, which may be a hard drive, solid-state hard drive, or any other suitable storage medium, device, integrated subsystem, and so forth.

Input-output interface also allows mobile device 116 to communicate with central processing unit 112 for the presentation of data input screens, audio alarms, and the transmission of data to the central processing unit 112. Interface 114 is thus an input and output device, and may comprise a wireless hub which would allow a large number of mobile devices such as mobile device 116 to communicate with central processing unit 112.

Central processing unit 112 may also be controlled by an algorithm which estimates application times for patient badges, and provides the position with a template for a treatment plan, optionally including suggestions at one or more points in the treatment plan template. Such template presented to a physician may be based on the particular details associated with the patient, such as age, preconditions, current ailment, and so forth. Such presentation allows the physician to limit his work to changing particular tasks in accordance with the judgment of the physician.

More particularly, in accordance with the invention, it is contemplated that treatment suggestions contained within the template will be presented in a bright color, such as bright red. Likewise, blanks may be indicated by a bright red line, yellow or green highlighting or the like. If the physician clicks on a suggested particular aspect of a treatment, the bright red alphanumeric representation of that aspect of the treatment changes to a different color, for example, black, indicating to the physician that that particular item has received the attention of the physician, directing the physician's attention to the next item. Alternately, clicking on a suggestion and typing in a change will also result in a black display of the physician's entry which replaces the template suggestion. The central database keeps track of what items have received attention and may use some or all of this information to send prompts or other informational units to appropriate persons subdatabase collections and/or tallies as the system may keep to monitor and/or improve the quality of medical services being delivered.

In order to provide a measure of reliability, it is contemplated that the presentation of a treatment plan to the physician, for example on a desktop personal computer, would be accompanied by a photograph of the face of the patient.

Likewise, central processing unit 112 is connected to patient badge printers 124 located, for example, at the point of admission of the patient and at the point of treatment, such as the most proximate nurse station. In accordance with one embodiment of the invention, it is contemplated that piezoelectric inkjet technology is used to generate sheets containing the inventive badges. This allows a wide variety of printing inks, such as the FDA approved inks produced by Colorcon, which are preferred in accordance with the invention.

Figure 15:
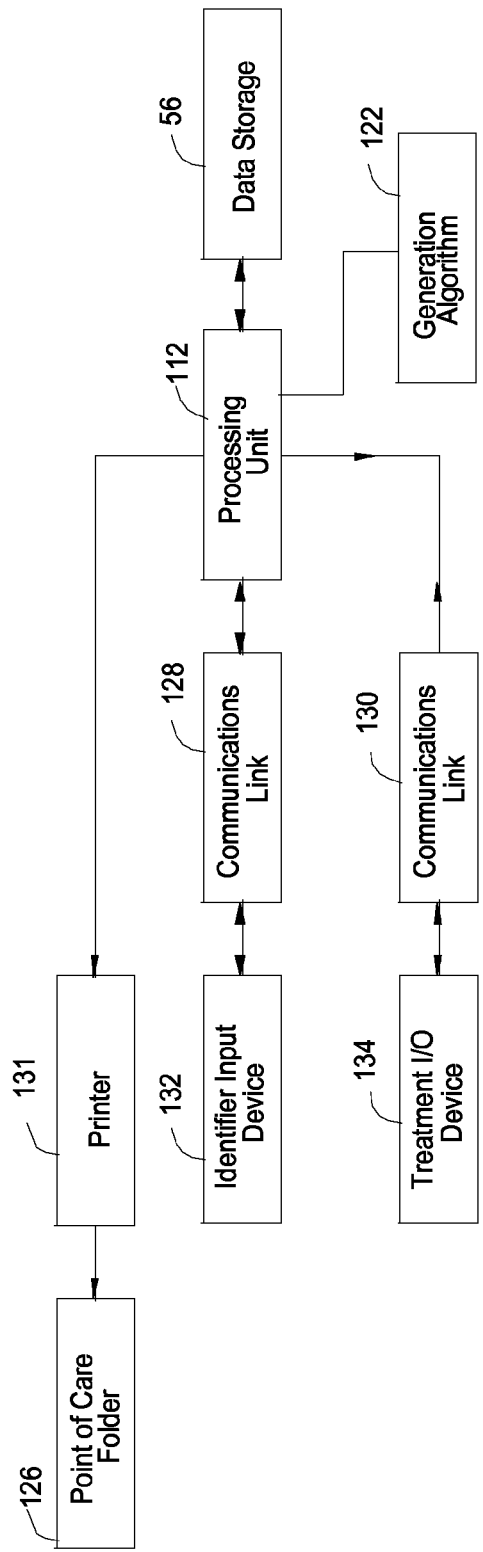
FIG. 15 is flow chart of a system that generates patient badges at the direction of central processing unit.

As illustrated in FIG. 15, the present invention envisages generation of patient badges, optionally at the direction of central processing unit 112, and, optionally, the placement of sheets bearing the patient badges in a point of care folder 126 proximate the patient and a printer 131. Printer 131 may be located proximate the patient at the time of printing, and this will provide an additional measure of protection at the time of application of the inventive patient badge.

As alluded to above, central processing unit 112 is connected, for example wirelessly, by wireless communication routers 128 and 132 to mobile devices 132 at the point of admission of the patient, and mobile devices 134 at the point of treatment of the patient.

In accordance with the invention, central processing unit 112 also generates an identification number and machine readable identification, such as a barcode, using generation algorithm 122. As described above, this information and other information input into the system is used by central processing unit 112 to generate a patient badge design which is stored, along with other information in data storage device 156.

Figure 16:
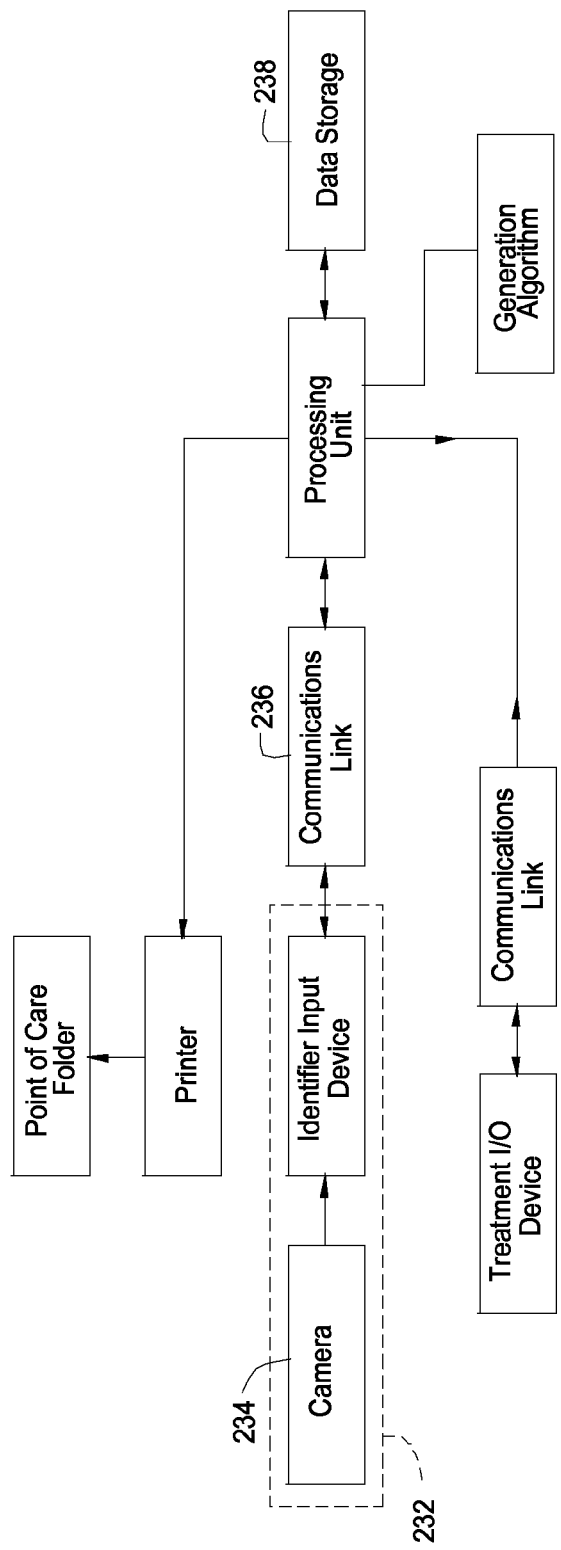
FIG. 16 is a flow chart of a system that generates patient badges with an input device that includes a camera used to take picture of a patient's face.

Referring to FIG. 16, a system similar to that of FIG. 15 is illustrated. However, in the embodiment of FIG. 16, input device 232 includes a camera 234 which may be used to take a picture of the face of the patient, for example at the time of patient intake. Such picture is advantageously taken before information received from the patient is entered into the system, and before doctor/healthcare worker inputs into the system. Such picture is then advantageously displayed on the information input device during information entry to reduce the possibility of error due to misidentification of patient during data entry. Advantageously, the picture of the patient and/or patient name optionally remains on the screen in a fixed position as information is input into the system, for example on a personal computer or mobile device, for example a mobile device with a touch screen (such as a smartphone with an application enabling the inventive system).

In accordance with the invention, it is contemplated that the patient admission area of the health facility will have on hand a number of input devices such as input device 232, which may take the form of a mini tablet, or full size tablet incorporating a camera and wireless conductivity to a wireless modem 236 located in the admission area. When a patient is being admitted, an input device 232 is given to the patient. The input device prompts the patient to fill in various informational units to be used by the system, such as the information being gathered at step 14 in FIG. 1. This information, including an image of the face of the patient, is directly transferred by the system for storage in data storage device 238.

In accordance with the preferred embodiment, it is contemplated that a patient may take his/her own picture using input device 232. Alternatively, a nurse may use the input device 232 to take the picture of the patient, as that is likely to ensure image quality and uniformity of presentation. In connection with the taking of the image of the patient, the display on input device 232 may include a rectangle within which the face of the patient should fit. This will assure uniformity of presentation, maximum information by maximizing the size of the face of the patient, and reduce the time necessary to compose the picture.

It is further contemplated in accordance with the invention that, in addition to a front view of the face of the patient, the healthcare professional at the point of admission may also take a profile view of the patient. Again, to promote uniformity, an indicator may be included on the display of the input device. Such indicator may take the form of a simple line profile to provide a guide and a template on which the profile of the patient may be superimposed. Thus, the individual taking the picture will see a live display of the picture which the camera on the input device will take, superimposed on a generalized profile represented, for example, by a single curved profile-like line, or a single such line plus an indication of the lips and eyes.

Figure 17:
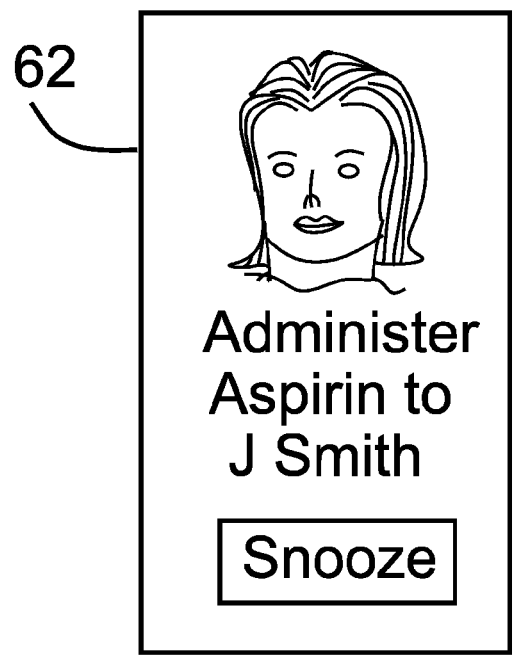
FIG. 17 illustrates the display of a mobile device which shows the patient's face and a prompt to administer certain care to the patient.
Figure 18:
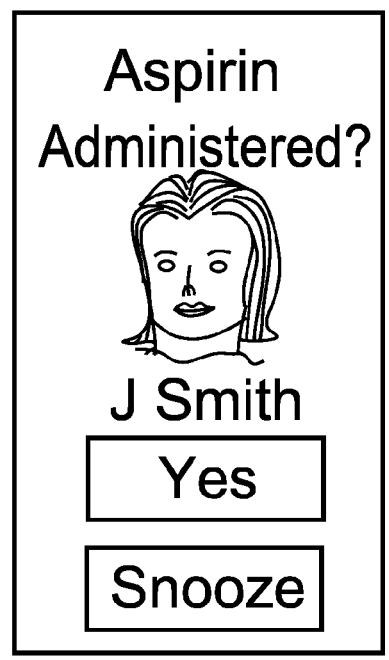
FIG. 18 illustrate the display of a mobile device where the display shows reminder and query prompts.

The system illustrated in FIG. 16 allows the presentation of the face and/or profile of the patient along with prompts to administer certain care to the patient, for example as illustrated in FIG. 17. Likewise, prompts may be included in reminder and query screens, as illustrated in FIG. 18. This will increase the likelihood of a correct input from the healthcare provider, due to the redundancy of identification information in photographic as well as alphanumeric form. This multiple presentation of information is useful due to varying abilities and speed with which individuals may recognize information in alphanumeric versus visual form, and potential complications that may be caused by fatigue, distraction, or the like.

Further in accordance with the invention, it is contemplated that patient image presentations may advantageously also be included on sheets of patient badges as an added safeguard to ensure that the patient is receiving one of his patient badges and not the patient badge of another person. While it may seem difficult that such a mistake can be made, it is possible that an individual may remove a patient badge sheet, be distracted by a task from completion of a patient badge application, and then, after the distraction, apply the patient badge to the wrong patient. The probability of such a mistake is reduced due to the presence of the image on the patient badge sheet, and, optionally, also on the patient badge being removed and replaced.

Likewise, even after a patient badge has been applied to the correct person, a distraction may occur requiring the immediate attention of the healthcare provider, after which, or during which the sheet with the remaining patient badges may be put down or placed in the wrong folder.

Figure 19:
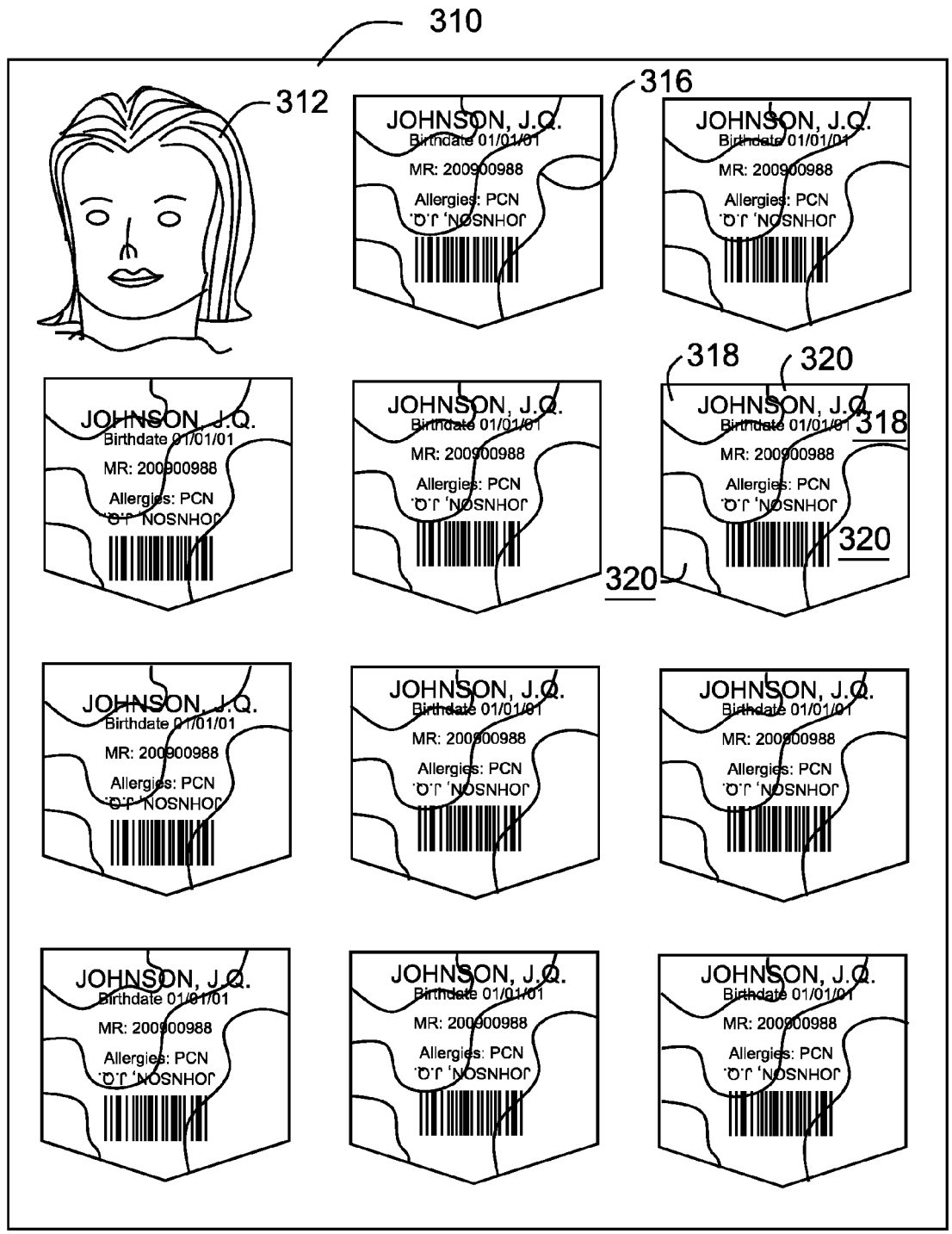
FIG. 19 is a diagram of a patient badge sheet with an image of the patient where the badge sheets include curved background areas.

Such a patient badge sheet 310 including the image 312 of the patient is illustrated in FIG. 19. The patient badges in patient badge sheet 310 also include curved background areas 316 which give an additional visual cue to people using the system, thus reducing the probability of mistake. In accordance with the invention, various patient badge backgrounds may be used, optionally consisting of a visual unique to the patient. Whether unique or not, the system may assign backgrounds that are clearly different to the various patients expect to be in proximity to each other. In accordance with the invention, the background of the patient badge may be divided into alternating areas 318 and 320, which may be colored with pale shades of similar colors. For example, areas 318 may be colored pale pea green and areas 320 may be colored pale bluish green. Other similar color pairs which may be included on a single patient badge may be, for example, amber/yellow, pale lavender/pale purple, pink/pale maroon, and the like.

Similar shades are used to send a clear color signal to the viewer, at the same time projecting a background shaped image to improve distinctiveness and recognition. Alternately, adjoining background areas may receive the same pale color, but have different degrees of intensity, for example a 10% benday or halftone adjacent a 15% benday or halftone.

Figure 20:
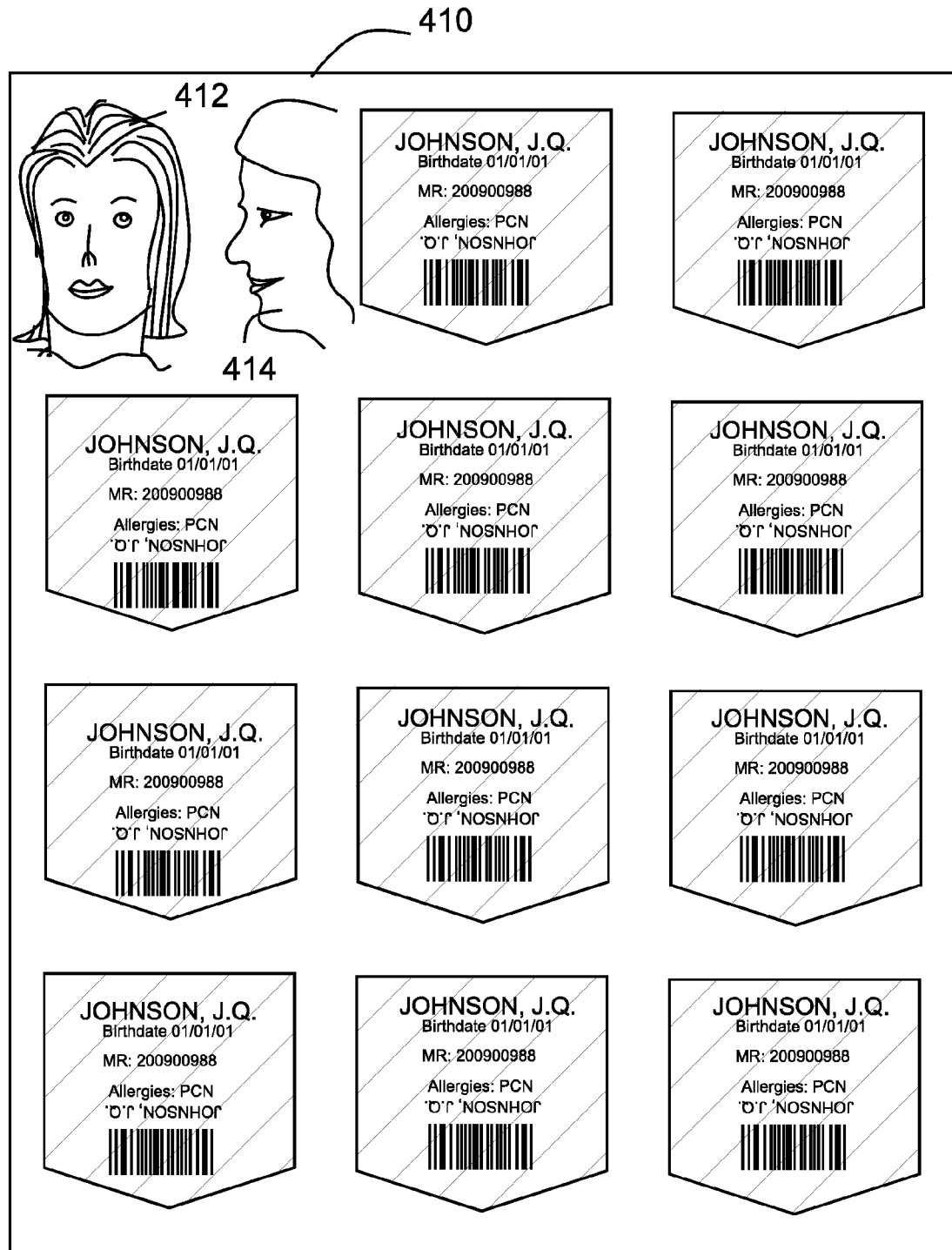
FIG. 20 is a diagram of a patient badge sheet which includes frontal and profile images of a patient where the background patter consist of a stripe patter of contrasting colors.

A patient badge sheet 410 similar to the patient badge sheet of FIG. 19 is illustrated in FIG. 20. However, the background pattern instead of forming curves is of a stripe pattern, likewise incorporating contrasting color stripes in alternating fashion. In addition to a frontal face image 412, patient badge sheet 410 includes a profile image 414.

Figure 21:
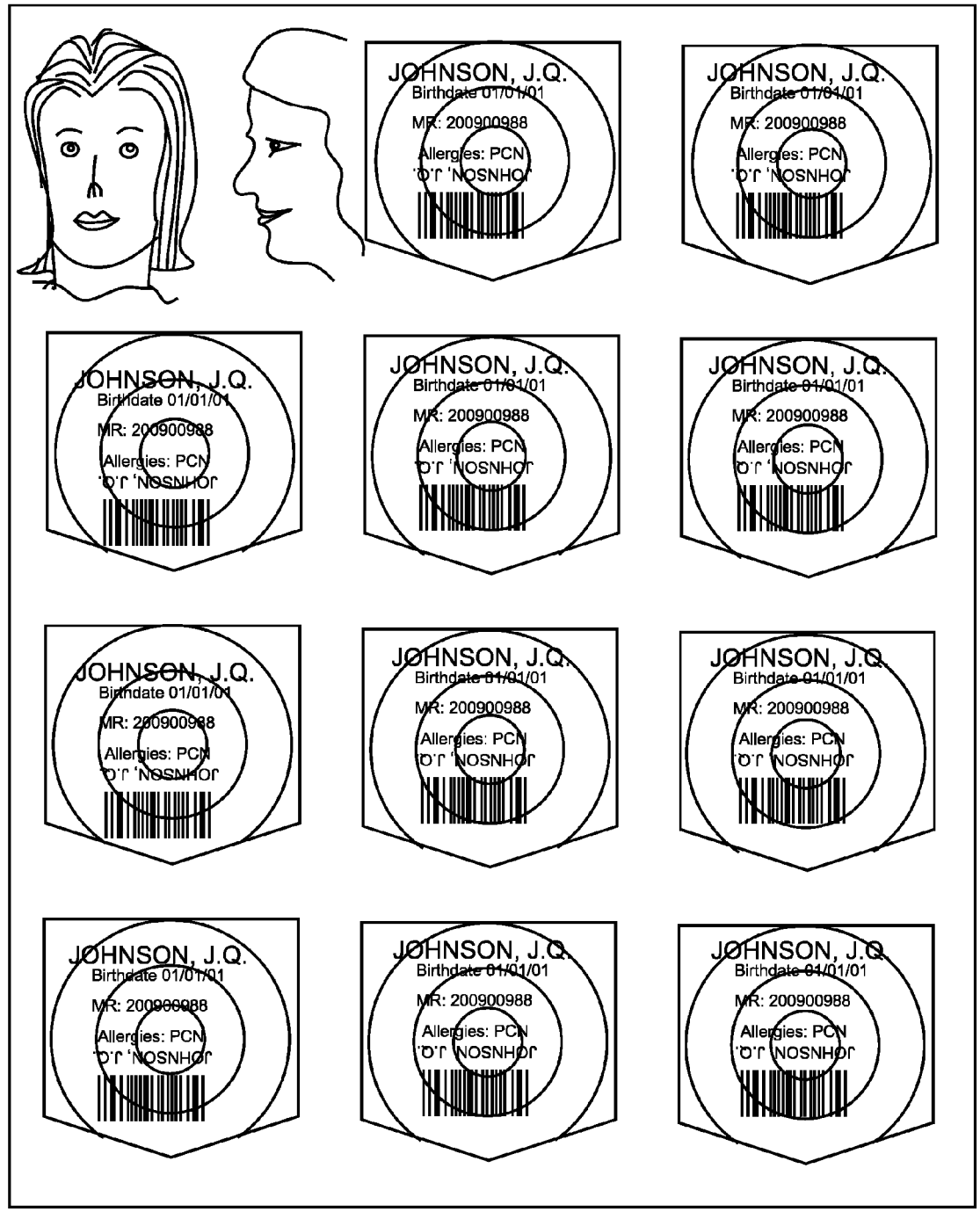
FIG. 21 is a diagram of a patient badge sheet which includes frontal and profile images of a patient where the background pattern is a target image.
Figure 22:
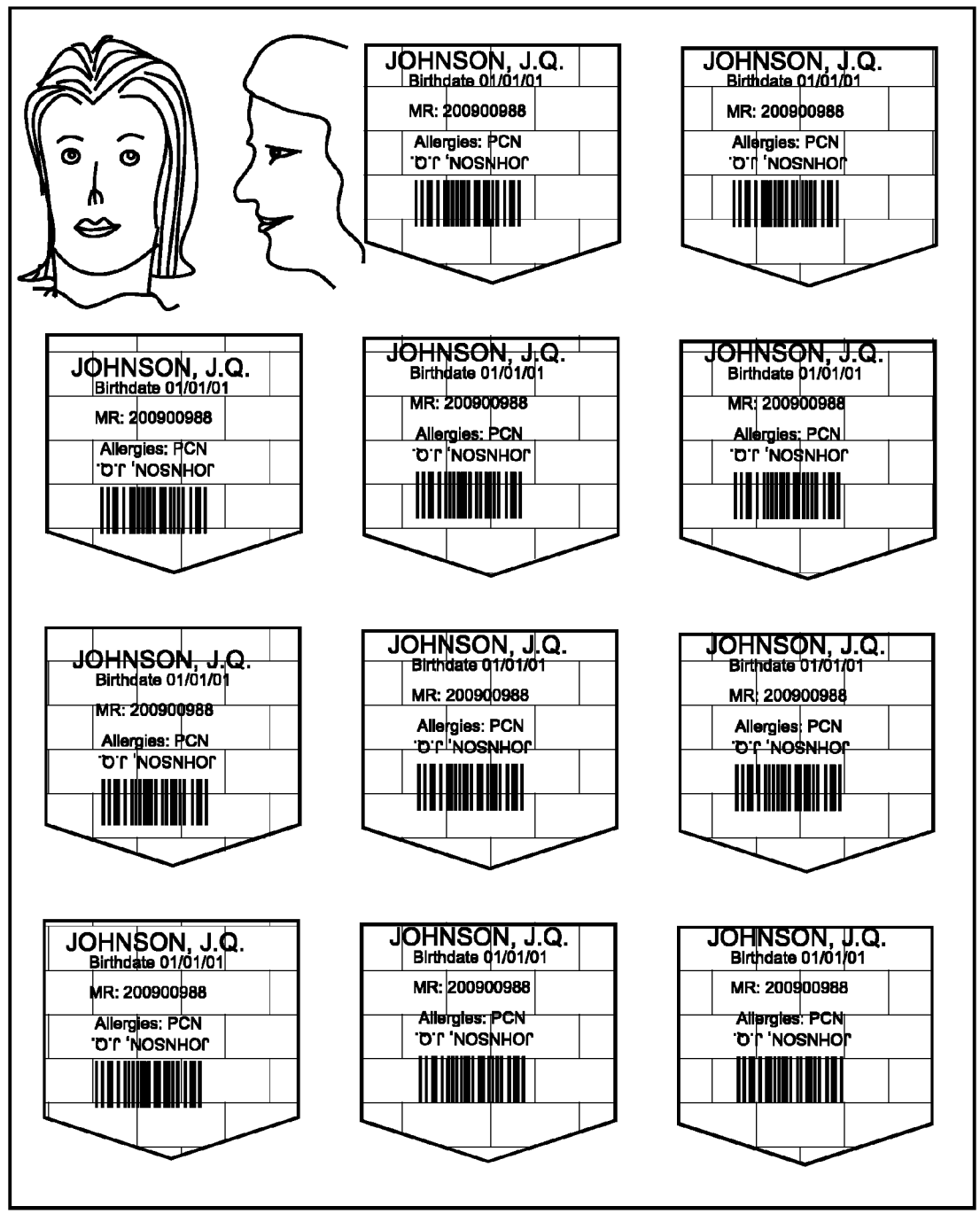
FIG. 22 is a diagram of a patient badge sheet which includes frontal and profile images of a patient where the background pattern comprises a brick pattern.

FIG. 21 illustrates a patient badge sheet similar to that of FIG. 20, except that the background pattern is a target image. FIG. 22 is similar to FIG. 21, except that the background pattern comprises a brick pattern. Other types of patterns are also possible, such as a teddy bear, sailboat, owl, apple, airplane, and so forth, and the patient may be offered several options from which to pick.

Figure 23:
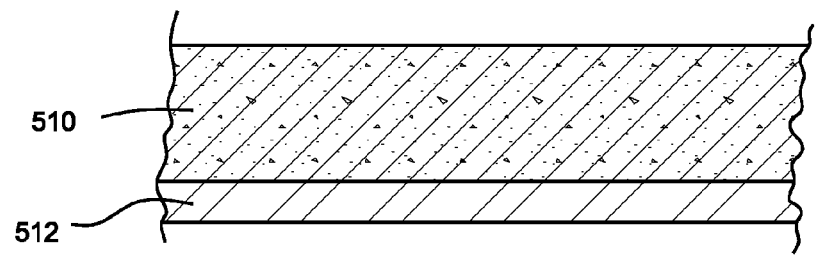
FIG. 23 is an image of a sheet of paper with coating that is used for receiving temporary cutaneous identification.

Referring to FIG. 23, a sheet of paper 510 for receiving a temporary cutaneous identification device image is illustrated. Sheet 510 bears a release coating 512.

Figure 24:
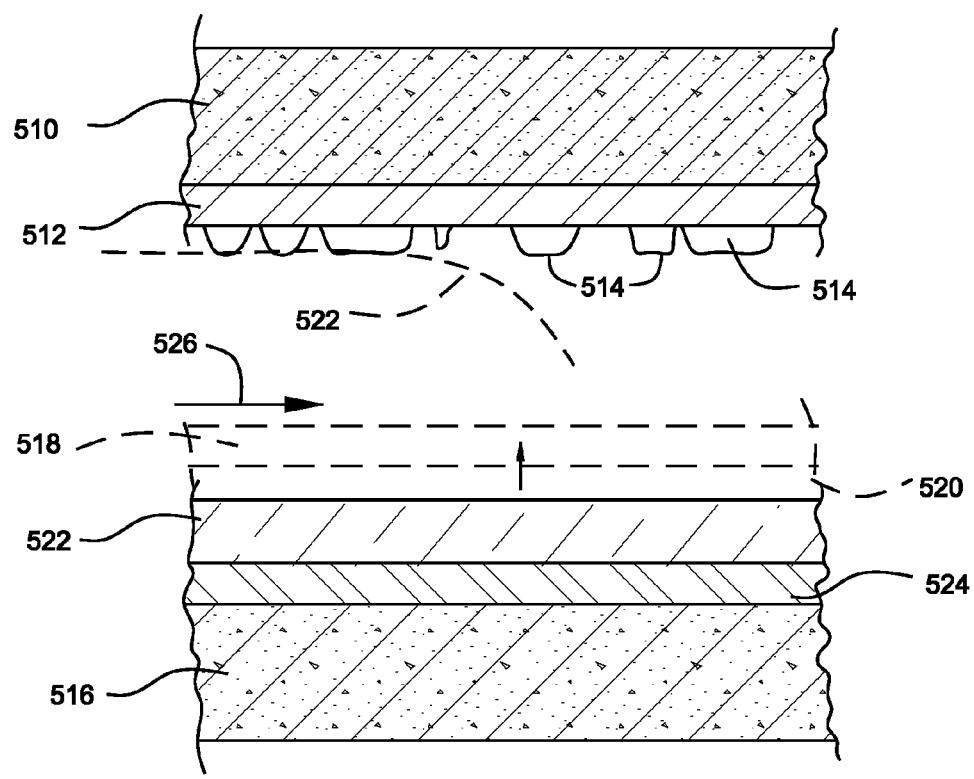
FIG. 24 illustrates two sheets, one sheet with coating that has ink deposits which adhere to the coating and another sheet that has a protective layer and an adhesive layer.

When it is desired to make a sheet of patient badges, sheet 510 with coating 512 is placed in a laser or inkjet printer and an image is deposited thereon. The image takes the form of deposits of ink 514, as illustrated in FIG. 24. Ink 514 is deposited on and adheres to release coating 512.

Figure 25:
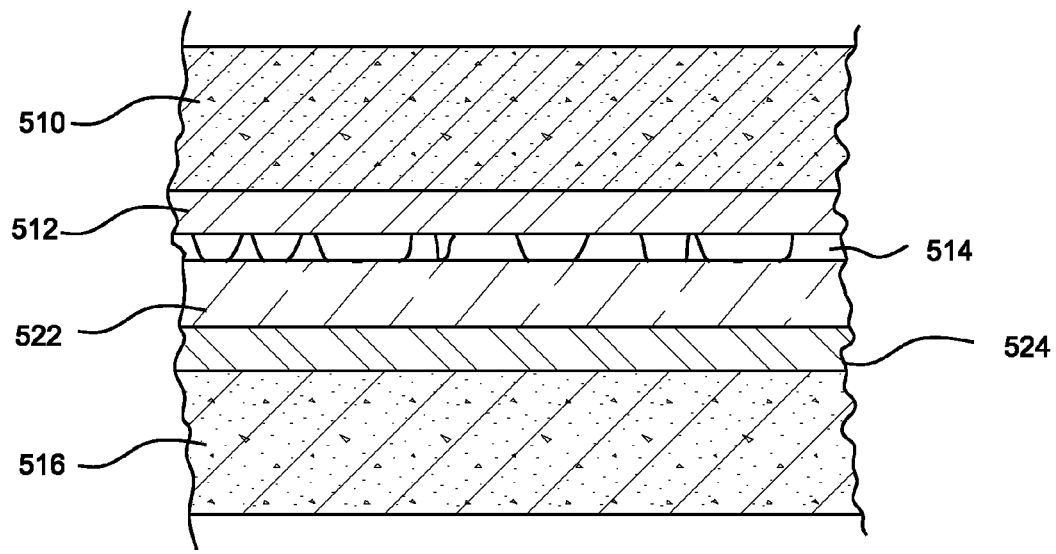
FIG. 25 illustrates a structure that results when one sheet with coating that has ink deposits comes in contact with an exposed adhesive layer of another sheet once a protective layer is taken off.

During the manufacture of a patient badge sheet, a second sheet of paper 516 is put proximate to and in facing spaced relationship to sheet 510 after a protective layer of paper 518 bearing a layer of release agent 520 has been removed. This allows a layer of adhesive 522 overlying a layer of release agent 524 to be exposed prior to assembly of the patient badge sheet, as illustrated in FIG. 24. In accordance with known techniques for the assembly of temporary tattoos, sheet 516 with exposed adhesive layer 522 disposed on it is curled as indicated in phantom lines adjacent ink 514. Sheet 516 is then adhered to one edge of sheet 510, and the curled surface of adhesive 522 is advanced in the direction of arrow 526 as illustrated in FIG. 24. The resulting structure is illustrated in FIG. 25.

Figure 26:
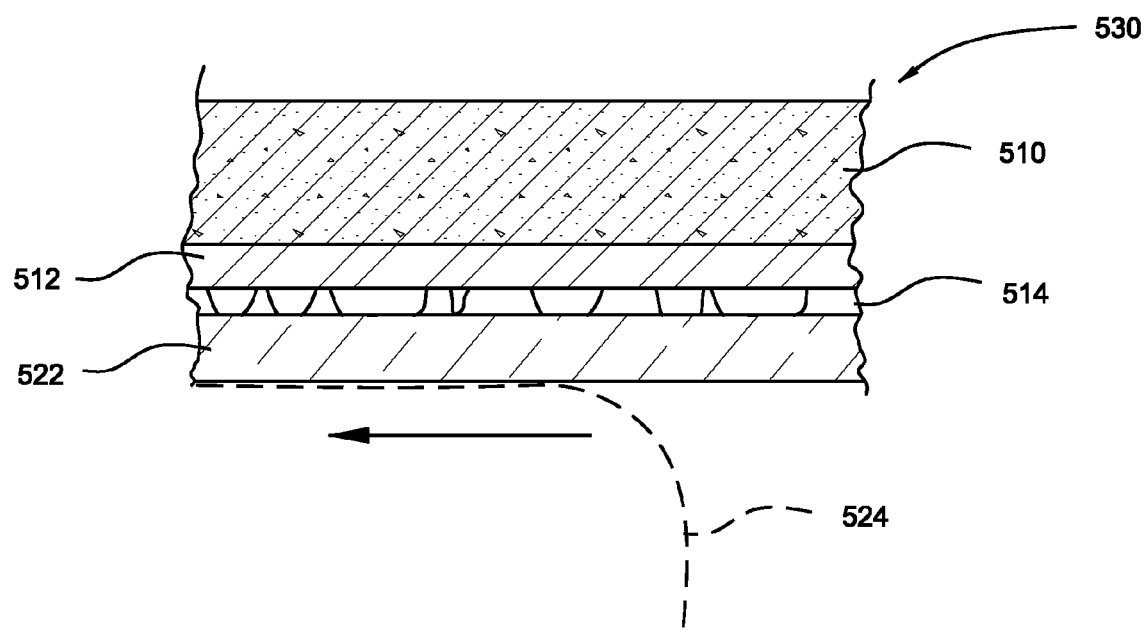
FIG. 26 illustrates a patient badge with a partially removed release layer.

When it is desired to apply a patient badge, a patient badge is separated from the sheet, for example by removing it from the sheet. To apply the patient badge, adhesive layer 522 must be exposed by removal of paper sheet 516 with release layer 524 by peeling the same way as illustrated in FIG. 26. The separated patient badge 530 may then be adhered to the skin of the patient in the manner of a temporary tattoo of conventional design.

After separated patient badge 530 has been adhered to the skin, it is possible to remove paper member 510 with release coating 512 because adhesive 522, transferred from sheet 516 to sheet 510, holds ink 514 more securely than release layer 512. This leaves adhesive 522 secured to the skin and ink 514 forming the desired patient badge image secured by adhesive 522 to the skin of the patient.

The manufacture of badge sheets is of relatively simple methodology. Accordingly, it is contemplated that such manufacture will occur both at the point of admission of the patient and at the point of care. Any structure and method of manufacture of the type used in the field of temporary tattoos may be employed to implement the methodology of the present invention.

Figure 27:
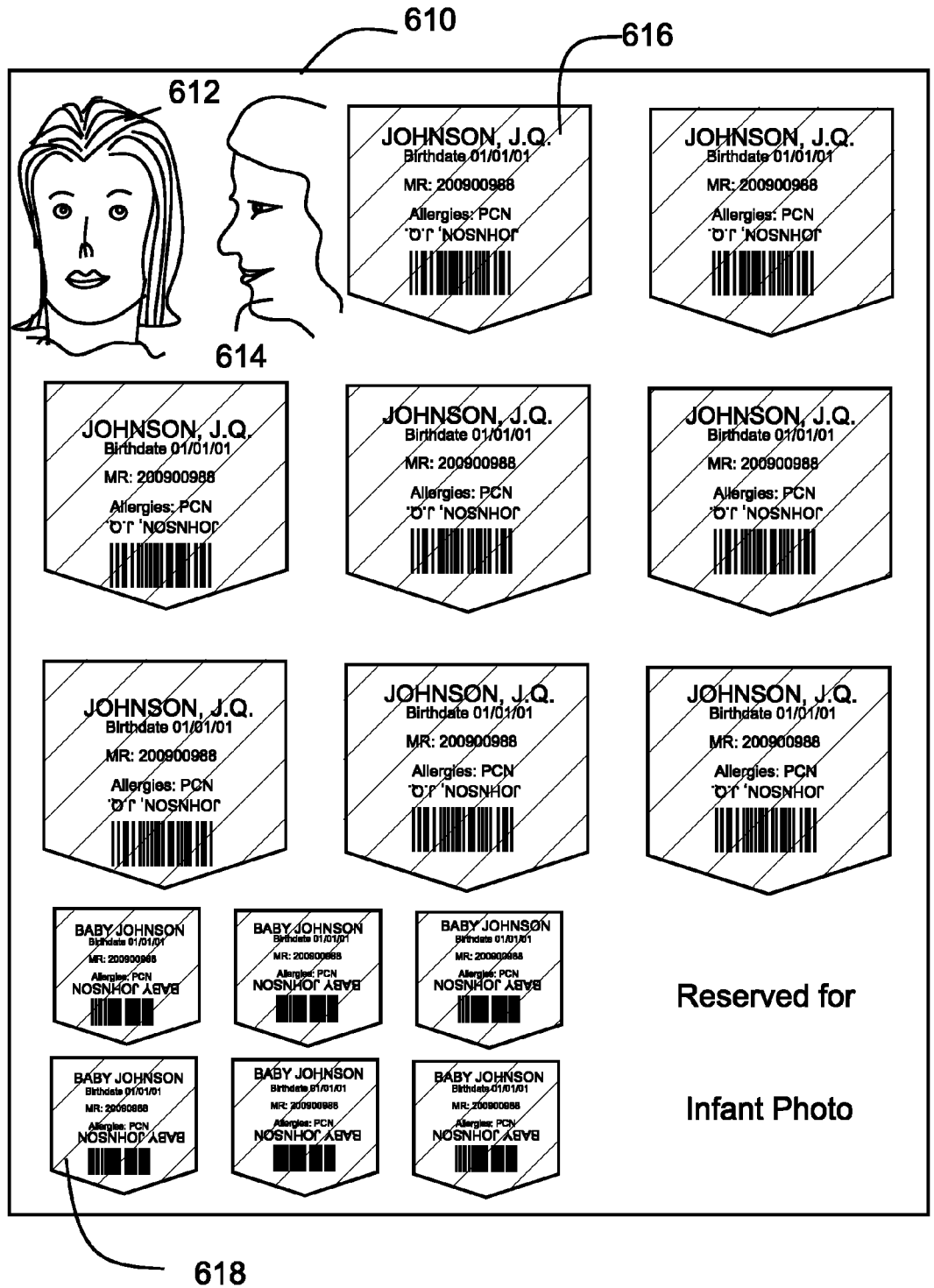
FIG. 27 is a diagram illustrating a plurality of patient badges generated on a single sheet including infant-sized and mother-sized patient badges, a picture of the mother, and reserved space for picture of the infant.

In accordance with the invention, it is contemplated that the inventive identification system will be of particular value in ensuring that mothers and babies are properly paired. More particularly, if a woman is being received for the purpose of childbirth, the system generates a specialized sheet including infant-sized and mother-sized patient badges and a picture of the mother. These specialized sheets, as illustrated in FIG. 27 are used during the hospital stay and ensure that mothers are properly paired with their babies. Such specialized sheets are located at the point of admission, and the points of care for the mother and the infant. Accordingly, when the child is born, the sheet 610 associated with the mother and located near the mother may be used to separate a baby-size patient badge 618 and apply it to the child, care being taken to see that the frontal face photo 612 and the profile 614 match the mother.

In accordance with the invention it is further contemplated that the mother will receive a patient badge 616 from the same sheet 610 at the time of the birth to further ensure proper correlation of child and parent. In the event that some irregularity should be revealed by the badging of the child and mother, DNA testing can avoid any mishap.

After the birth, the space on sheet 610 reserved for the infant's photo is filled with the photo of the infant. In accordance with the invention it is preferred that photos included on patient badge sheets be in color for ease and reliability of identification.

In accordance with a particularly preferred embodiment of the invention, patient badges are manufactured using glow-in-the-dark components, to provide for identification of a patient in the dark. This has the advantage of making it unnecessary to disturb patients by turning on lights during sleep. Moreover, it may also save time in emergency situations.

Patient badges may be made to glow in the dark by several techniques. For example, glow-in-the-dark pigments may be mixed into the adhesive which remains on the skin of the patient while the badge is being worn. Such phosphor pigments may be of any color, and may be used for color coding purposes. Green phosphors are preferred for their longer persistence, although blue phosphors have the advantage of brighter light emission.

It is also possible to mix glow-in-the-dark phosphor pigments with transparent thermoplastic toner material to make a glow-in-the-dark toner for laser printers. Additional versatility may be achieved by using transparent tinted red, blue and yellow phosphorescent toner pigment formulations with a black pigment formulation. In this case the black pigment formulation would be of conventional design and would be used to depict alphanumeric and/or image data, while the glow-in-the-dark pigments may be used for tinted backgrounds, identification background patterns, and so forth. Still another possibility is to utilize a five toner cartridge laser printer where four of the toner cartridges are of conventional design and the fifth toner cartridge contains a phosphorescent toner formulation which acts as a light source to improve visibility in the dark.

Figure 28:
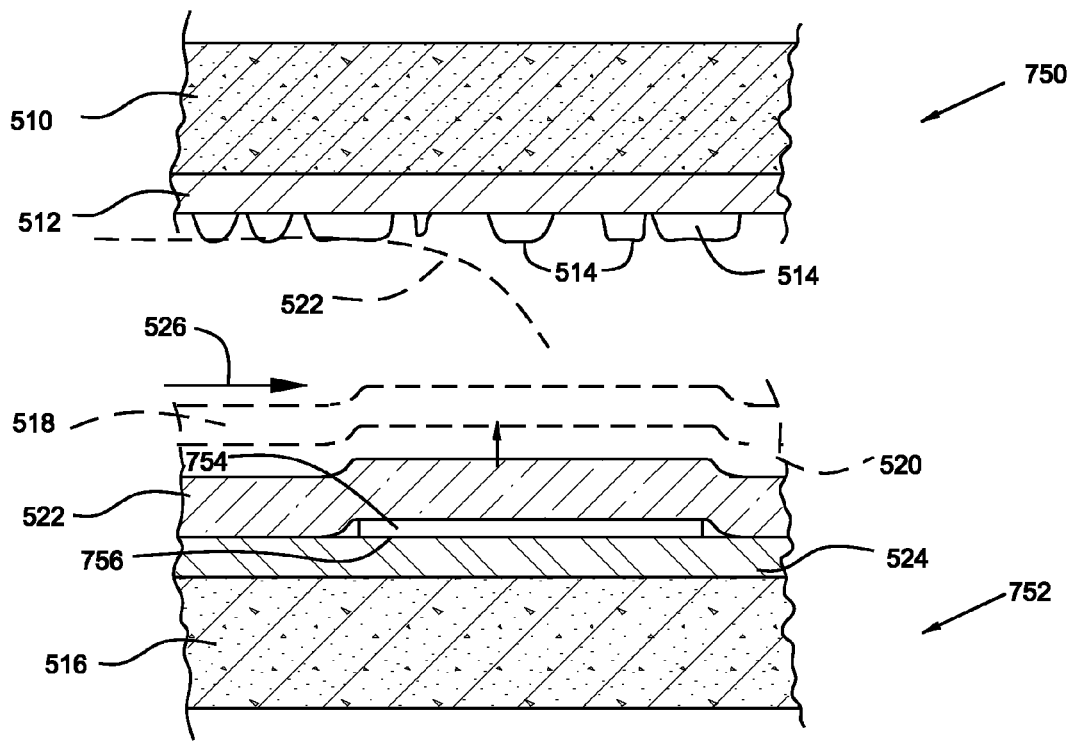
FIG. 28 illustrates a paper image receiving sheet with a release coating and ink deposits and an adhesive sheet.

As discussed above, badges may be manufactured in a health facility, such as a hospital, by staff using materials commonly available for tattoo generation. Generally, as illustrated in FIG. 28, image receiving sheet 750 made of paper 510 with a release coating 512 is printed with laser or inkjet type ink deposits 514. Image bearing sheet 750 then transfers the ink only to an adhesive sheet 752 by being put into contact with its adhesive layer 522.

In contrast to the sheets illustrated in FIG. 24 which form a badge, an RFID chip 754 may be employed. Chip 754 may be an active RFID chip, a passive RFID chip, or any other device capable of acting as a transponder. While passive ISAM band chips operating in the 865-868 MHz range in Europe and the 902-928 MHz range in North America are preferred because of their low cost, typically in the range of $0.15 each, other technologies may be used, including active devices, devices operating in the 3 to 10 GHz range, devices acting in lower microwave frequency ranges, UHF devices of the type operating in the range of about 433 MHz, as well as high-frequency and low-frequency devices. Choice depends upon cost, range desired, and data speed required. However, in accordance with the invention, relatively slow data speeds will provide substantially acceptable functionality for the system described herein.

Figure 29:
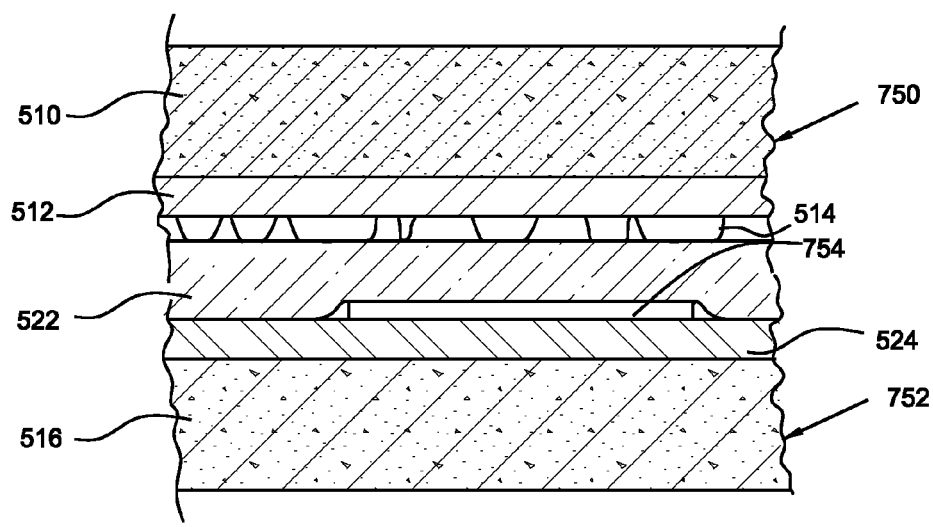
FIG. 29 is an assembly illustration of an image bearing sheet being in contact with an adhesive bearing sheet where the adhesive is contacting the image ink.
Figure 30:
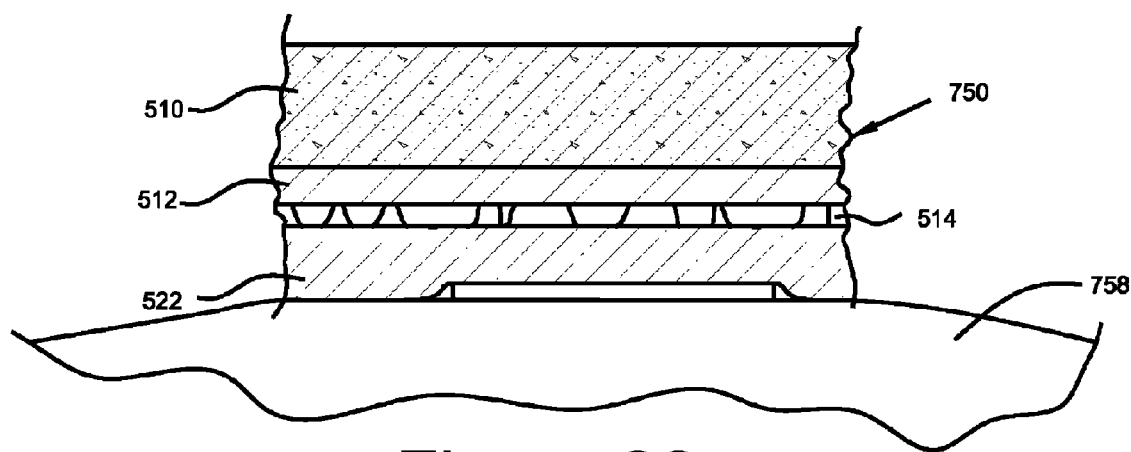
FIG. 30 illustrates the image ink that was transferred to the adhesive layer come in contact with patient's skin.
Figure 31:
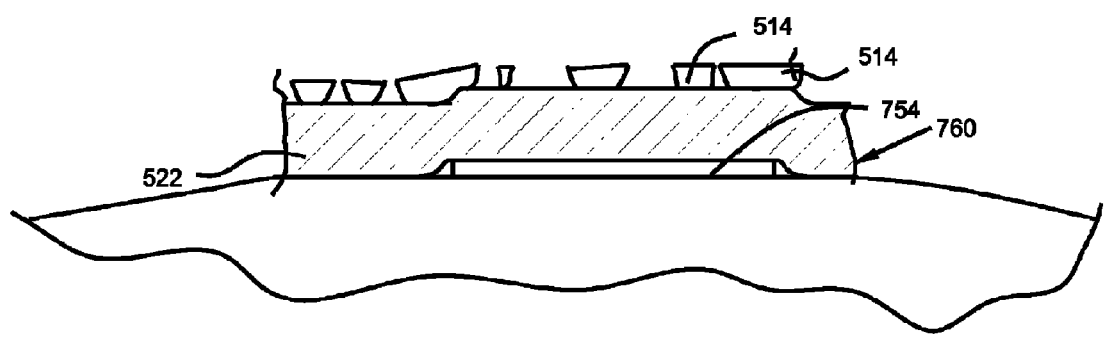
FIG. 31 illustrates an applied identifier.

As illustrated in FIG. 28, image bearing sheet 750 is brought into contact with adhesive bearing sheet 752, with adhesive 522 contacting image ink 514, as shown in FIG. 29. Sheets 750 and 752 are then pulled apart resulting in a transfer of the image ink 514 to adhesive layer 522. This arrangement is shown in FIG. 30. In accordance with a preferred embodiment, a quantity of adhesive is deposited on the underside 756 of RFID chip 754, as illustrated in FIG. 28. This facilitates adhesion of the assembly of sheet 752 to skin 758 of a patient.

Such patient badges may be removed by any technique used for the removal of temporary tattoos, such as rubbing with mineral oil, alcohol and so forth.

Figure 32:
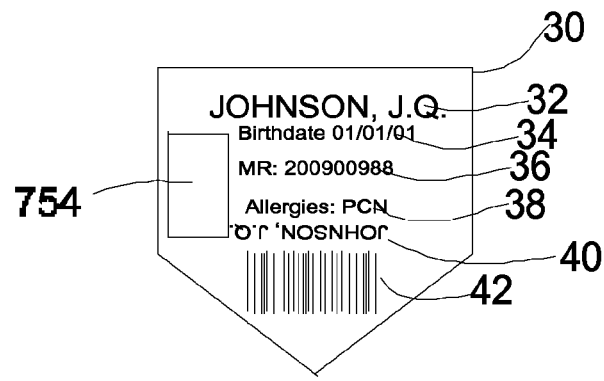
FIG. 32 is an image of a badge that is formed as a result of releasing the paper and coating from the badge assembly.

Moisture may then be applied to paper layer 510, resulting in the release of the assembly of paper layer 510 and release coating 512 from the badge assembly, leaving behind patient badge 760. The resulting badge is shown in FIG. 32.

Figure 33:
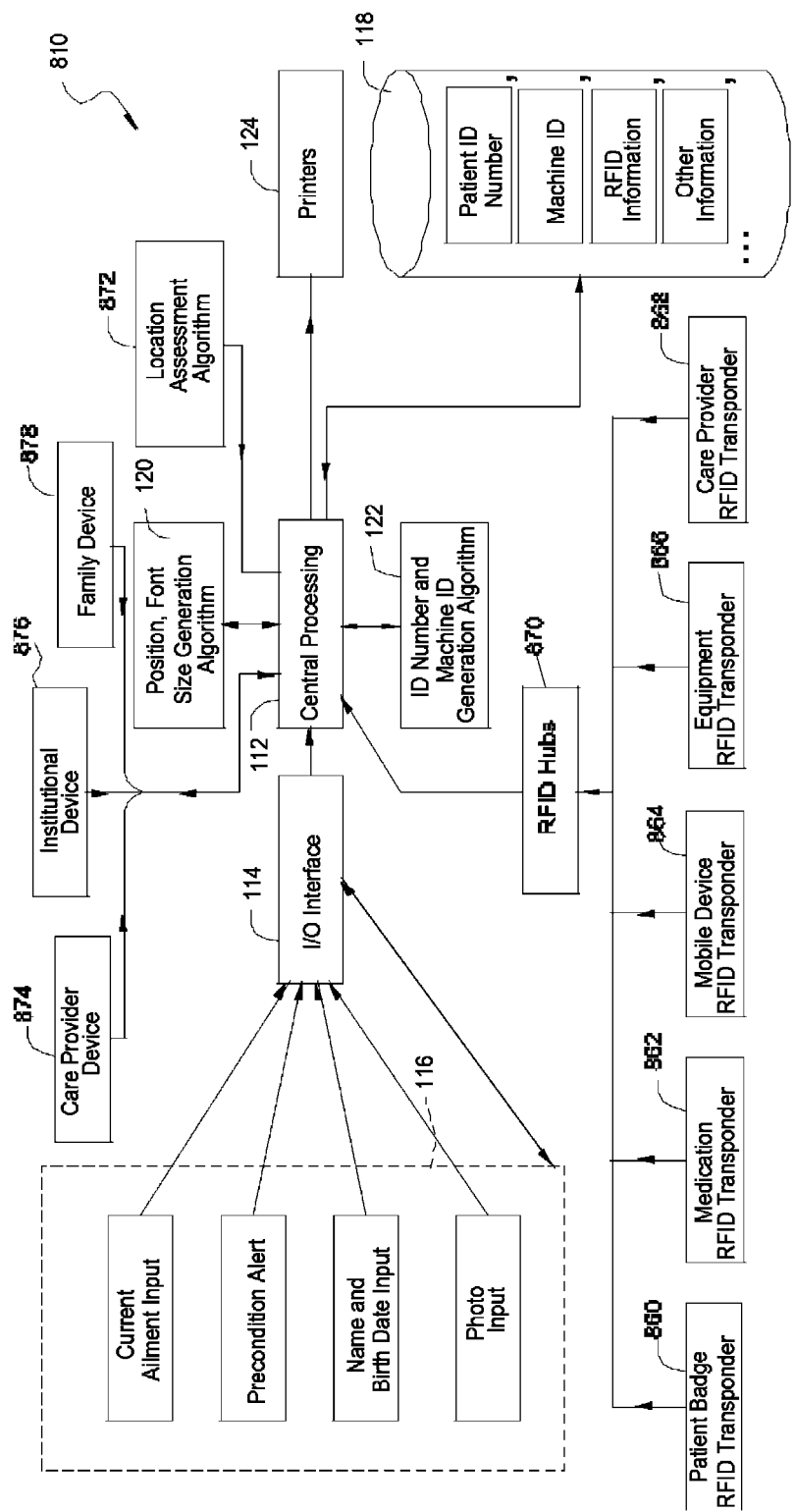
FIG. 33 illustrates an inventive system that uses RFID information.

Referring to FIG. 33, one embodiment of the inventive system 810 using RFID information is illustrated. The operation of the system of FIG. 33 is similar to that of the system of FIG. 14, except for the addition of processing and use of RFID information. More particularly, information respecting location of patients is gathered from patient badges 860.

Location information for bottles or packages of medication bearing RFID tags 862 is also gathered by the system. Similar information for the location of caretaker mobile devices is collected at transponder 864 which is attached to the respective mobile device. Equipment whose location may change receives an RFID transponder 866. Similarly, care providers may advantageously be provided with badges, such as clip on badges of a permanent nature bearing RFID transponders 868. This may indicate the absence of needed personnel in a given area or be used to determine which healthcare provider may be messaged or alarmed to proceed to a given area to address a need or critical need, for example one generated from the system in response to the system's monitoring instrumentation connected to a patient or historical data respecting a patient, advantageously, for example, monitoring of such information using an artificial intelligence algorithm.

In accordance with the invention information from transponders 860-868 is sent by way of RFID hubs 870. Hubs 870 may be placed at various locations, for example, in the patient's room, and a nursing station, and so forth. The range of RFID hubs 870 may be varied. For example, an RFID hub attached to the bed of the patient may have a range limited to the immediate vicinity of the bed. In this manner, it may determine which bottles of medication pairing RFID transponders 862 have entered the vicinity of the patient's bed. This information is relayed to central processing unit 112 for storage in storage device 118. Periodically, all location information is processed by algorithm 872 which uses the location information to detect potential problems.

Figure 34:
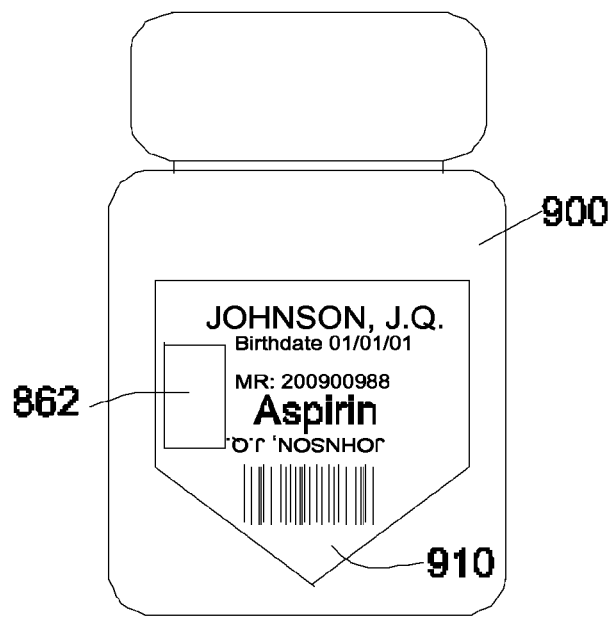
FIG. 34 is an image of a badge bearing a RFID transponder along with the patient's information.

For example, if a bottle 900 of penicillin bearing RFID transponder 862 (FIG. 34), on a badge 910 which may be a simple adhesive sticker optionally bearing the name of the patient, is detected close to the bed of a patient who is allergic to penicillin, this information would be assessed by algorithm 872 and could result in the transmission of an alarm to the mobile device 874 of a care provider. If the matter is serious enough, an alarm may also be transmitted to an institutional device, such as a nurse's station, a personal computer 876 in the hospital administration, and so forth, to receive supervisory attention at the appropriate level. Such alerts may be sent simultaneously or in staggered fashion, as deemed necessary. All received information and responses are stored in the system as a protection against potential legal liability.

In accordance with the invention it is also contemplated that RFID information may be used for other purposes. For example, the personal computer of the family of a patient, or a smart phone 878 owned by a family member may be signaled when, for example, a patient's location has changed from the operating theater to the patient's room, by emailing a message to smart phone 878 saying that the family member has been moved from the operating room to a private room and, optionally, giving or confirming the location of that room. The message may further indicate that visitation may be had at certain hours.

In accordance with the invention, such information may also be segregated and analyzed, for example, developing profiles for healthcare providers, departments, particular types of medical procedures, and so forth.

Thus, the ability may be provided to provide a badge which carries an RFID chip (or some other technology). This may be used to set off an alarm if a child is removed from a designated area. Also, the same may advantageously be used as a potential "tracker" so that hospital staff know where a patient is on a floor or in a building.

Likewise, the above system may be merged with physiologic sensing technologies to create a patient ID that not only conveys identification and medical information, but also engages in real time, wirelessly transmitted, physiologic sensing and databasing of information, i.e., morning blood draws to find out the patients blood chemistry status, etc. for example, a colorimetric oxygen sensor may be incorporated into the inventive badge, and applied to the chest of the patient.

It may thus be seen that patient specific information can be input into the system and the software will configure it to meet the design criteria of the patient badge.

The configured information is transmitted to a desktop printer located in the healthcare facility, either in an admitting area or on in a patient care area (e.g., nurses station, emergency department, etc.).

The selected patient badges may be applied to the patient in a wide variety of positions, for example, the front of the neck just above the superior sternal notch, the dorsal surface of the foot, and the center of the upper back just below the neck.

In accordance with a preferred embodiment, patient badges are applied using a "peel packed" water impregnated foam pad designed to cover the temporary cutaneous identification device fully, and with sufficient aqueous solution that several temporary coetaneous identification devices can be applied with a single pad, but without so much aqueous phase as to drip or run. Such wet sponges, pads or the like may be packaged in any suitable container, such as double foil heat sealed containers of the type used to contain perfumes, condiments, and so forth.

As alluded to above, if the patient has an electronic medical record at the health care facility, a barcode, and/or a quadratic residue code, and/or an RFID microdot or microchip may be incorporated into the patient badge so that a link to more detailed information can be made immediately accessible using a reader device appropriate for the device or code.

The inventive patient identification badge can also be easily removed using a "peel pace" foam sponge impregnated with a solution capable of dissolving the adhesive of the inventive temporary coetaneous identification device without irritating the skin (e.g., mineral oil, baby oil, Detatchol™, etc.).

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. A method of identifying a patient and providing information respecting said patient comprising:
    (a) obtaining identification information;
    (b) obtaining patient associated information;
    (c) depositing on an adhesive member ink in a visually interpretable configuration conveying to a human user said identification information and said patient associated information;

(d) applying said adhesive layer to said patient;
(e) applying a machine-readable identification device to said adhesive layer;
(f) inputting healthcare related information associated with a patient into a database by entering said healthcare related information onto a mobile device electronically coupled to said database;
(g) reading said machine-readable identification device using a mobile device;
(h) outputting onto said mobile device patient care related information in response to the reading of said machine-readable identification device by said mobile device;
(i) receiving treatment information into said database;
j) outputting from said database to a mobile device treatment information respecting a particular healthcare service;
(k) receiving from said mobile device an indication that said healthcare service has been performed; and
(l) after a period of time following up to confirm performance of said healthcare service if the same has not been reported to the database as being performed.

2. A method as in claim 1, further comprising sending an alarm to another database if confirmation of performance of a particular healthcare service has not been received by the database.

3. A method as in claim 1, wherein an image of the patient is stored in the database and the output of said patient care related information is accompanied by a picture of the patient on said mobile device.

4. A method as in claim 1, wherein said adhesive member receives a deposit of background ink in a unique configuration.

5. A method as in claim 1, wherein a plurality of adhesive members are formed on a single sheet and are applied to the patient at different times.

6. A method of identifying a patient and providing information respecting said patient, comprising:
(a) obtaining identification information;
(b) obtaining patient associated information;
(c) depositing on an adhesive member ink in a visually interpretable configuration conveying to a human user said identification information and said patient associated information; and
(d) applying said adhesive layer to said patient
wherein adhesive members meant as badges for a mother and other adhesive members meant as badges for a baby to be born are deposited at the same time on a single carrier sheet.

7. A method as in claim 6, where in adhesive members for a baby and its mother hard applied to the mother and the baby at the time of birth.

8. A method of identifying a patient and providing information respecting said patient comprising:
(a) obtaining identification information;
(b) obtaining patient associated information;
(c) depositing on an adhesive member ink in a visually interpretable configuration conveying to a human user said identification information and said patient associated information;
(d) applying said adhesive layer to said patient;
(e) applying, a machine-readable identification device to said adhesive layer;
(f) inputting healthcare related information associated with a patient into a database by entering said healthcare related information onto a mobile device electronically coupled to said database;
(g) reading said machine-readable identification device using a mobile device;
(h) outputting onto said mobile device patient care related information in response to the reading of said machine-readable identification device by said mobile device;
(i) applying an adhesive member with a machine-readable identification device to a medication;
j) receiving location information from said machine-readable identification device applied to a medication; and
(k) monitoring location of said medication and comparing such location information to expected locations for said medication to detect the likelihood of a dangerous situation due to the failure of the medication to be in a location where it is expected to be located.

\* \* \* \* \*